(12) United States Patent
Zannis et al.

(10) Patent No.: US 9,113,954 B2
(45) Date of Patent: Aug. 25, 2015

(54) COORDINATE INSTRUMENT SET

(75) Inventors: Anthony D. Zannis, Fort Wayne, IN (US); Herbert E. Schwartz, Fort Wayne, IN (US); Prasanna Malaviya, Mason, OH (US); Keith M. McGrath, Warsaw, IN (US); Danny E. McAdams, Warsaw, IN (US); Andrew M. Jacobs, Fort Wayne, IN (US); Jack Farr, II, Indianapolis, IN (US); Randall L. Holcomb, Memphis, TN (US)

(73) Assignee: DEPUY SYNTHES PRODUCTS, INC.

( * ) Notice: Subject to any disclaimer, the term of this patent is extended or adjusted under 35 U.S.C. 154(b) by 149 days.

(21) Appl. No.: 13/428,319

(22) Filed: Mar. 23, 2012

(65) Prior Publication Data

US 2012/0191015 A1 Jul. 26, 2012

Related U.S. Application Data

(62) Division of application No. 11/261,839, filed on Oct. 28, 2005, now abandoned.

(60) Provisional application No. 60/623,624, filed on Oct. 29, 2004.

(51) Int. Cl.
*A61B 5/00* (2006.01)
*A61B 19/00* (2006.01)
*A61B 5/107* (2006.01)
*A61B 17/00* (2006.01)

(52) U.S. Cl.
CPC .............. *A61B 19/46* (2013.01); *A61B 5/1076* (2013.01); *A61B 5/4514* (2013.01); *A61B 5/4528* (2013.01); *A61B 2017/00867* (2013.01); *A61B 2019/444* (2013.01); *A61B 2019/461* (2013.01)

(58) Field of Classification Search
USPC ................... 33/402, 427, 464; 600/550, 587; 606/102
See application file for complete search history.

(56) References Cited

U.S. PATENT DOCUMENTS

| 1,365,484 A | 1/1921 | Greenwald |
| 1,703,736 A | 2/1929 | Jacob |
| 2,597,644 A | 5/1952 | Johnson |
| 2,598,858 A | 6/1952 | Thomas |
| 2,770,046 A | 11/1956 | Wichmann |
| 3,704,707 A * | 12/1972 | Halloran ......................... 606/97 |
| 3,835,854 A | 9/1974 | Jewett |

(Continued)

OTHER PUBLICATIONS

Hesbmat Shabriairee and Charles Erichsen, O'Connor's Textbook of Arthroscopic Surgery, 2nd ed., 1992, Chapter 19, pp. 227-246.

(Continued)

*Primary Examiner* — Sean Dougherty

(57) ABSTRACT

Surgical instruments for use in mapping tissue defects include telescoping rulers and tubes. One of the instruments has a pointed anchoring tip for piercing tissue near the site of the defect. Another instrument has a hook for catching an anatomical landmark. Measuring portions of the rulers of both instruments include distance indicia so that a coordinate system can be established for mapping the location of the defect or of an implant at the defect site. The coordinate system can be re-established at a later time using the same fixation point for the anchoring tip and the same landmark for the hook to evaluate the clinical effects of the treatment selected. The method of using the instrument set is also described.

10 Claims, 14 Drawing Sheets

(56) References Cited

U.S. PATENT DOCUMENTS

| | | | |
|---|---|---|---|
| 3,955,073 A | 5/1976 | Carew | |
| 4,016,867 A * | 4/1977 | King et al. | 600/591 |
| 4,078,625 A * | 3/1978 | Loeb | 177/233 |
| 4,571,243 A * | 2/1986 | Froning et al. | 604/116 |
| 4,573,270 A | 3/1986 | D'Amico | |
| 4,616,656 A * | 10/1986 | Nicholson et al. | 600/300 |
| 4,873,976 A | 10/1989 | Schreiber | |
| 4,880,429 A | 11/1989 | Stone | |
| 5,007,934 A | 4/1991 | Stone | |
| 5,108,438 A | 4/1992 | Stone | |
| 5,119,521 A | 6/1992 | Clontz | |
| 5,171,248 A * | 12/1992 | Ellis | 606/102 |
| 5,186,180 A * | 2/1993 | Bellas | 600/591 |
| 5,197,465 A * | 3/1993 | Montgomery | 128/207.29 |
| 5,226,428 A * | 7/1993 | Lee | 600/590 |
| 5,306,311 A | 4/1994 | Stone | |
| 5,312,351 A * | 5/1994 | Gerrone | 604/117 |
| 5,320,608 A * | 6/1994 | Gerrone | 604/117 |
| 5,320,633 A | 6/1994 | Allen | |
| 5,346,498 A | 9/1994 | Greelis | |
| 5,374,268 A | 12/1994 | Sander | |
| 5,403,264 A * | 4/1995 | Wohlers et al. | 600/32 |
| 5,469,524 A * | 11/1995 | Esch et al. | 385/118 |
| 5,556,410 A * | 9/1996 | Mittermeir et al. | 606/185 |
| 5,569,252 A | 10/1996 | Justin | |
| 5,681,353 A | 10/1997 | Li | |
| 5,702,462 A | 12/1997 | Oberlander | |
| 5,735,903 A | 4/1998 | Li | |
| 5,759,194 A | 6/1998 | Hammerslag | |
| 5,845,617 A | 12/1998 | Sager | |
| 5,860,923 A * | 1/1999 | Lenker et al. | 600/433 |
| 5,980,524 A | 11/1999 | Justin | |
| 5,993,475 A | 11/1999 | Lin | |
| 6,033,430 A * | 3/2000 | Bonutti | 606/232 |
| 6,042,610 A | 3/2000 | Li | |
| 6,056,778 A | 5/2000 | Grafton | |
| 6,152,935 A | 11/2000 | Kammerer | |
| 6,156,044 A | 12/2000 | Kammerer | |
| 6,159,167 A * | 12/2000 | Hardin-Naser | 600/587 |
| 6,159,179 A * | 12/2000 | Simonson | 604/117 |
| 6,293,961 B2 | 9/2001 | Schwartz | |
| 6,306,156 B1 | 10/2001 | Clark | |
| 6,306,159 B1 | 10/2001 | Schwartz | |
| 6,319,271 B1 | 11/2001 | Schwartz | |
| 6,425,887 B1 * | 7/2002 | McGuckin et al. | 604/272 |
| 6,427,351 B1 | 8/2002 | Matthews | |
| 6,428,562 B2 * | 8/2002 | Bonutti | 606/232 |
| 6,467,612 B1 * | 10/2002 | Rosenfeld | 206/63.3 |
| 6,494,848 B1 * | 12/2002 | Sommercorn et al. | 600/587 |
| 6,524,259 B2 * | 2/2003 | Baxter-Jones et al. | 600/591 |
| 6,575,921 B2 * | 6/2003 | Vanden Hoek et al. | 600/587 |
| 6,585,143 B1 * | 7/2003 | Schultz | 227/147 |
| 6,752,154 B2 * | 6/2004 | Fogarty et al. | 128/899 |
| 6,764,453 B2 * | 7/2004 | Meier | 600/587 |
| 6,802,817 B2 * | 10/2004 | Baxter-Jones et al. | 600/591 |
| 6,994,678 B2 * | 2/2006 | Baxter-Jones et al. | 600/591 |
| 7,004,959 B2 * | 2/2006 | Bonutti | 606/232 |
| 7,052,511 B2 | 5/2006 | Weldon | |
| 7,163,563 B2 | 1/2007 | Schwartz | |
| 7,166,112 B2 * | 1/2007 | Hawkins et al. | 606/102 |
| 7,201,917 B2 | 4/2007 | Malaviya | |
| 7,326,236 B2 | 2/2008 | Andreas | |
| 7,401,413 B1 * | 7/2008 | Nelson | 33/512 |
| 7,434,325 B2 * | 10/2008 | Foley et al. | 33/512 |
| 7,559,941 B2 | 7/2009 | Zannis et al. | |
| 7,563,266 B2 | 7/2009 | Camino et al. | |
| 7,819,918 B2 | 10/2010 | Malaviya | |
| 7,914,808 B2 | 3/2011 | Malaviya | |
| 8,012,205 B2 | 9/2011 | Plouhar | |
| 8,025,896 B2 | 9/2011 | Malaviya | |
| 8,308,662 B2 * | 11/2012 | Lo | 600/587 |
| 8,657,295 B2 * | 2/2014 | Ashton-Miller et al. | 273/446 |
| 2001/0002440 A1 * | 5/2001 | Bonutti | 606/232 |
| 2001/0005940 A1 * | 7/2001 | Schwarz | 30/123 |
| 2001/0034953 A1 * | 11/2001 | Cole, III | 33/668 |
| 2002/0111567 A1 * | 8/2002 | Vanden Hoek et al. | 600/587 |
| 2002/0115910 A1 * | 8/2002 | Diokno et al. | 600/220 |
| 2002/0193830 A1 * | 12/2002 | Bonutti | 606/232 |
| 2003/0021827 A1 | 1/2003 | Malaviya | |
| 2003/0023316 A1 | 1/2003 | Brown | |
| 2003/0032961 A1 | 2/2003 | Pelo | |
| 2003/0033021 A1 | 2/2003 | Plouhar | |
| 2003/0033022 A1 | 2/2003 | Plouhar | |
| 2003/0036797 A1 | 2/2003 | Malaviya | |
| 2003/0044444 A1 | 3/2003 | Malaviya | |
| 2003/0049299 A1 | 3/2003 | Malaviya | |
| 2003/0078617 A1 | 4/2003 | Schwartz | |
| 2003/0083594 A1 * | 5/2003 | Sommercorn et al. | 600/587 |
| 2003/0158502 A1 * | 8/2003 | Baxter-Jones et al. | 600/591 |
| 2003/0204204 A1 * | 10/2003 | Bonutti | 606/232 |
| 2003/0225344 A1 | 12/2003 | Miller | |
| 2004/0055203 A1 * | 3/2004 | Grayson | 43/4 |
| 2004/0181150 A1 | 9/2004 | Evans | |
| 2005/0027215 A1 * | 2/2005 | Baxter-Jones et al. | 600/591 |
| 2005/0148902 A1 | 7/2005 | Minar | |
| 2006/0211953 A1 * | 9/2006 | Zannis et al. | 600/587 |
| 2012/0191015 A1 * | 7/2012 | Zannis et al. | 600/587 |

OTHER PUBLICATIONS

PCT International Search Report Application No. PCT/US05/38919, dated Jun. 13, 2008.

* cited by examiner

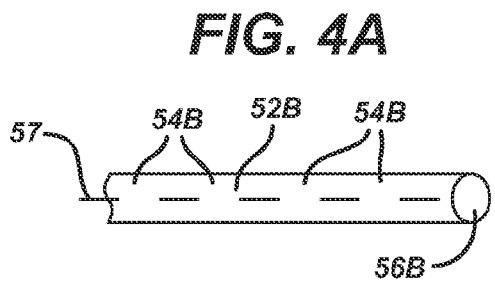
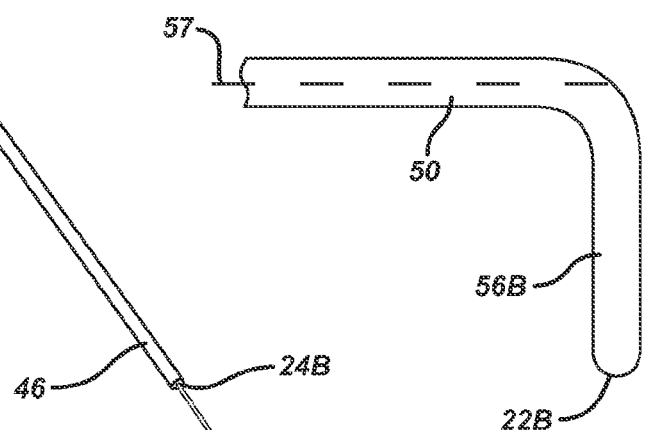
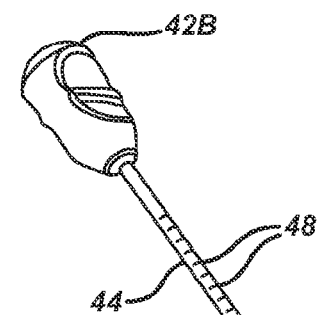
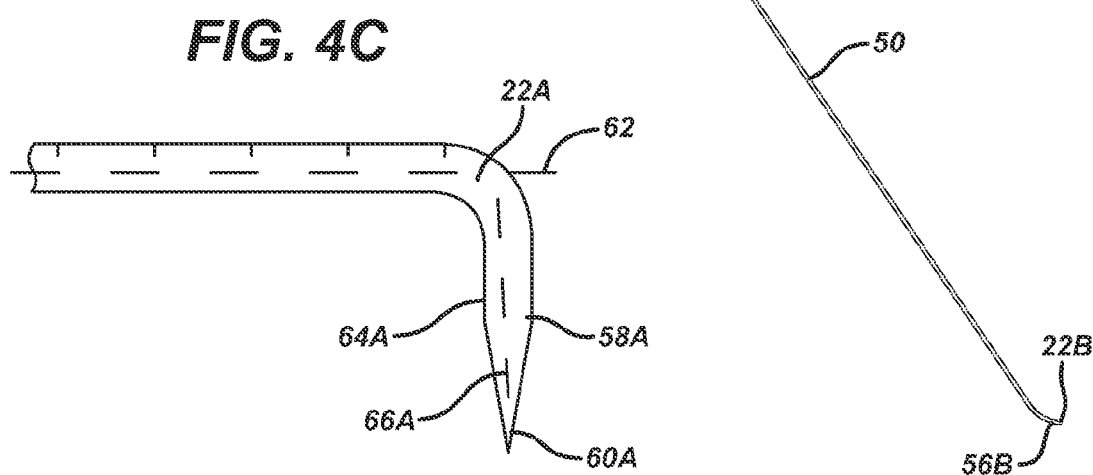

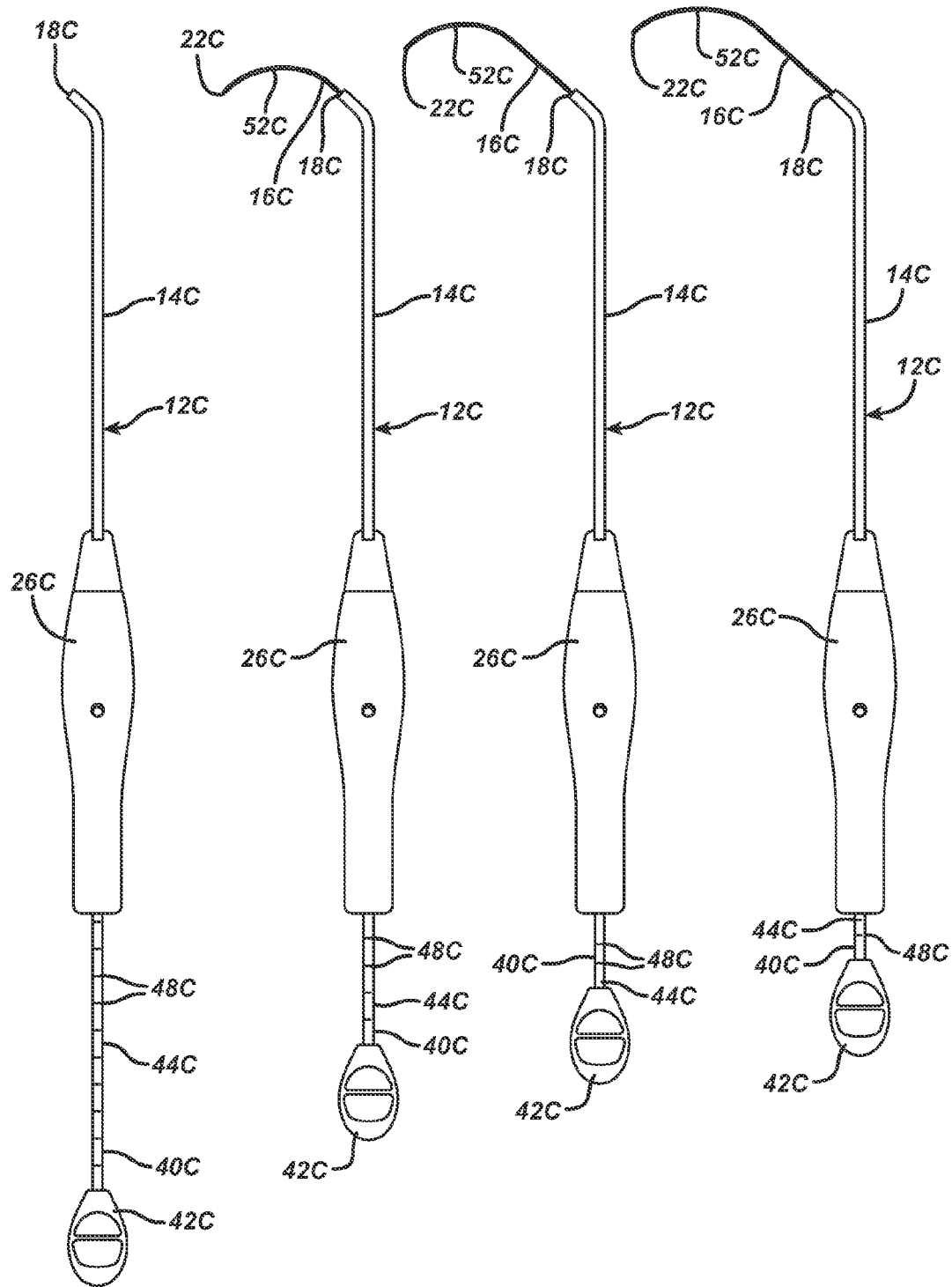

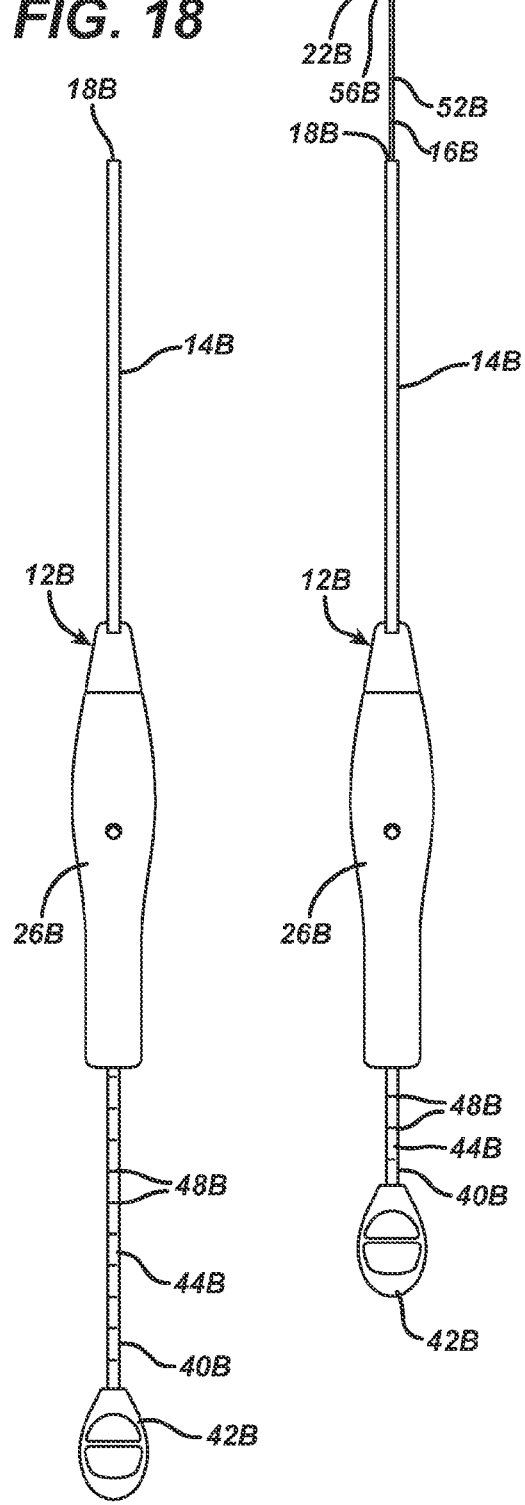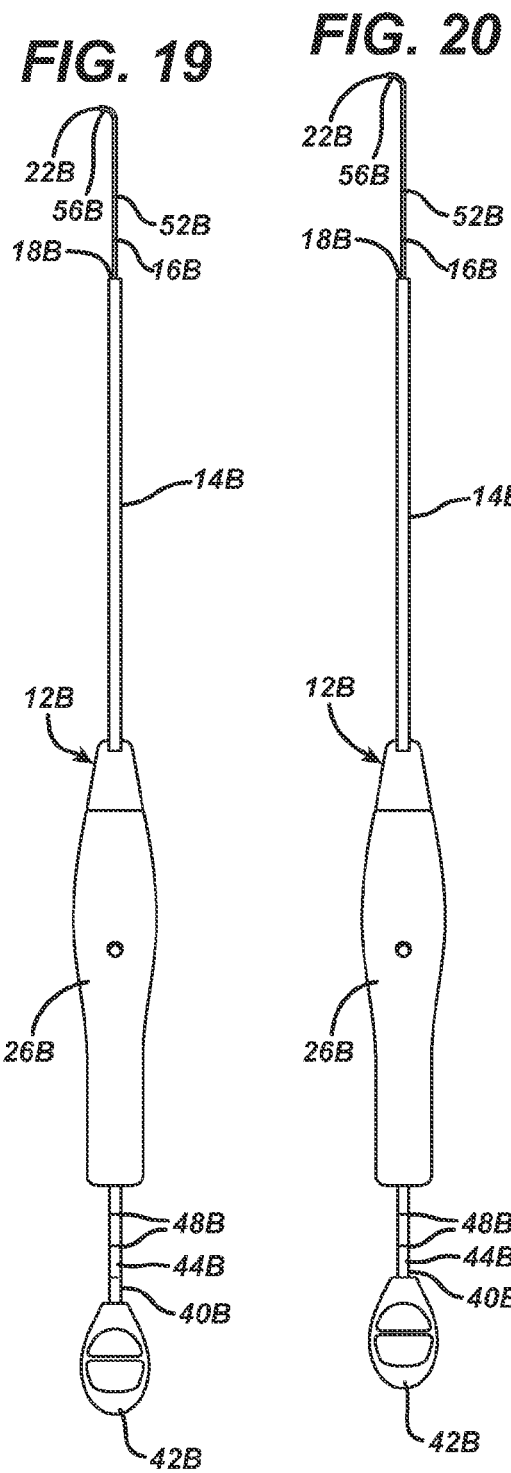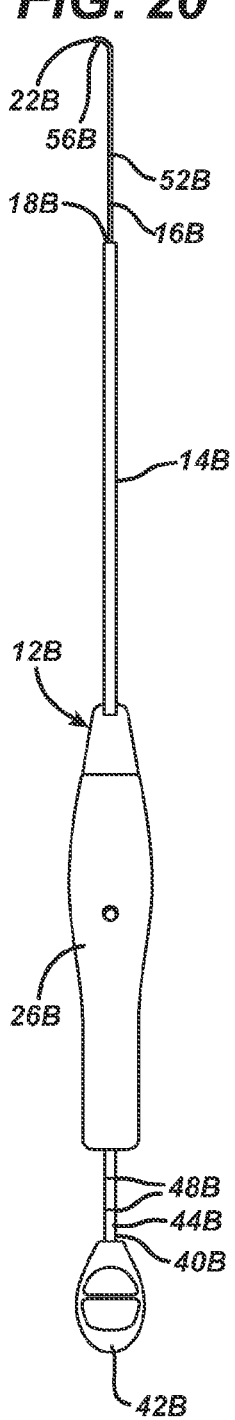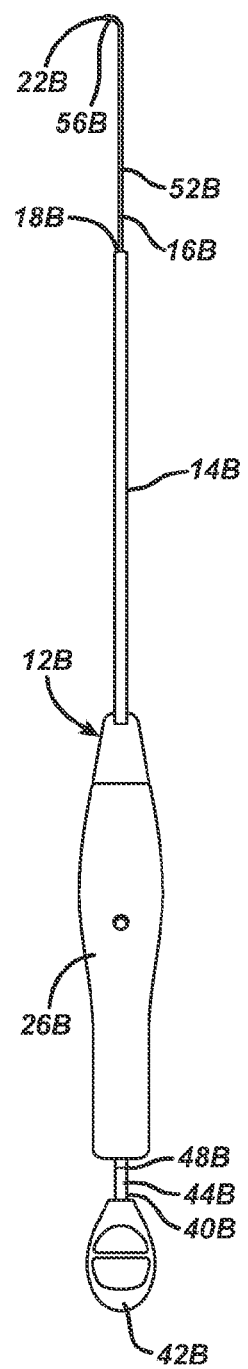

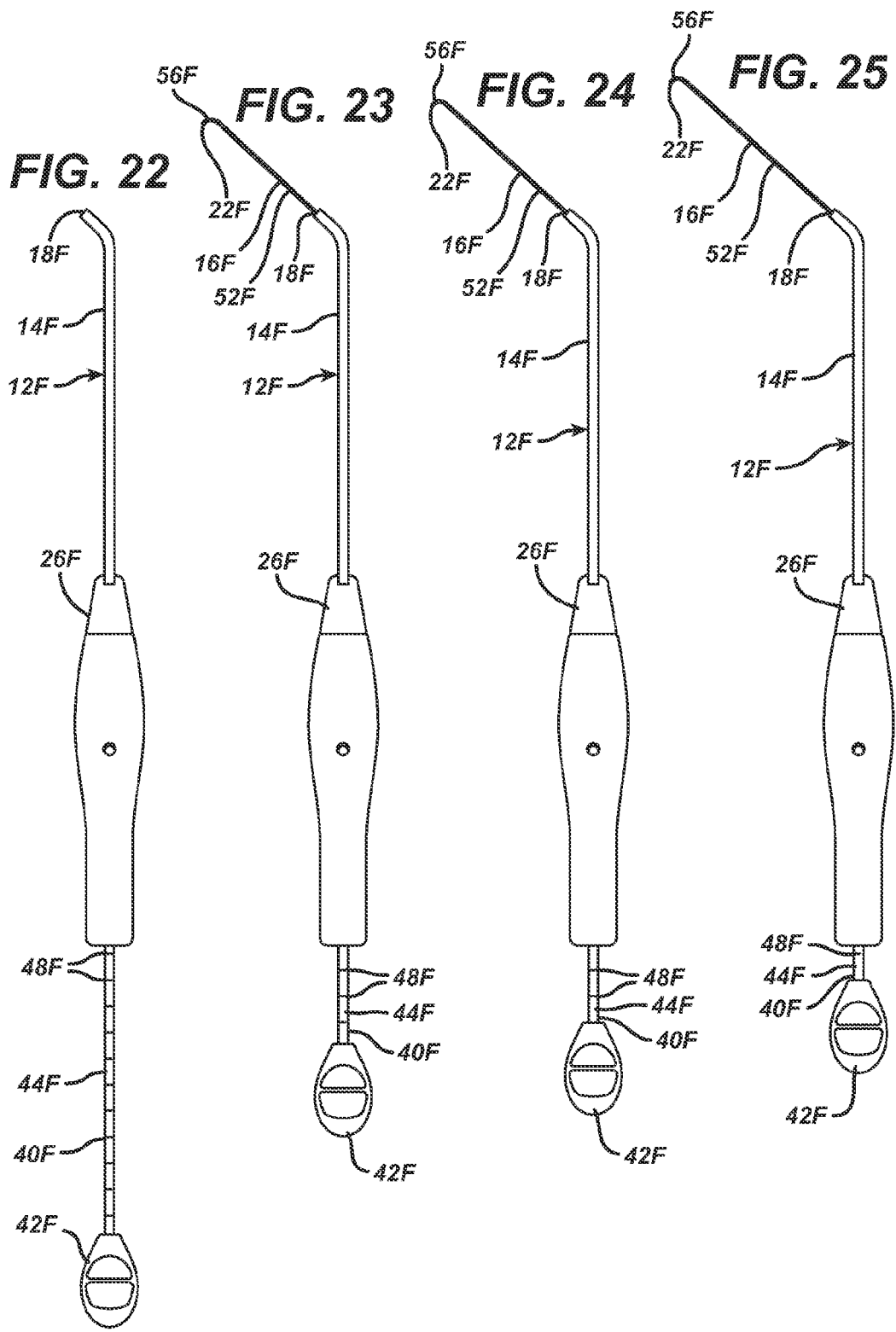

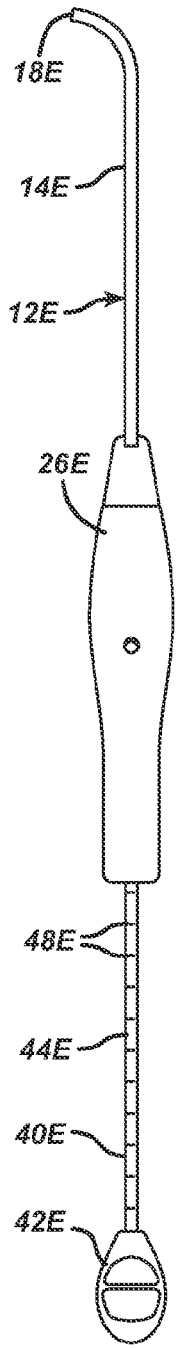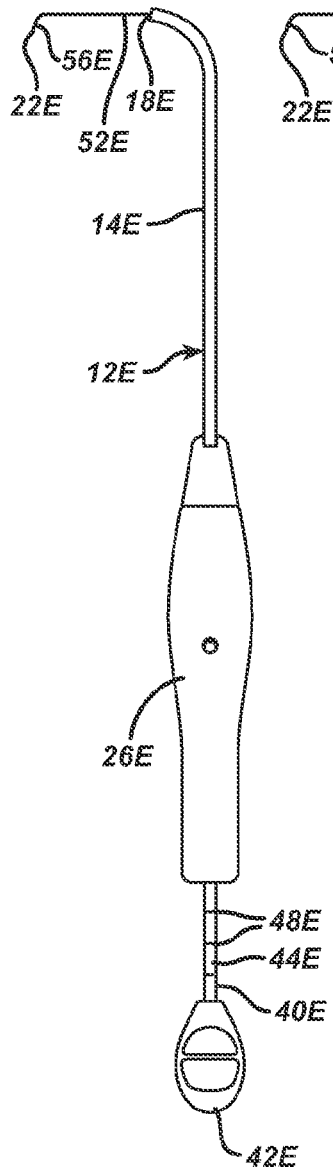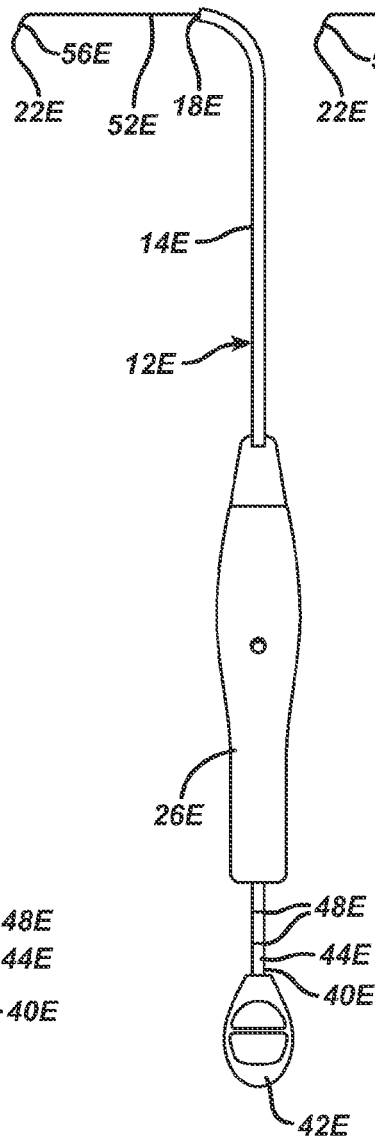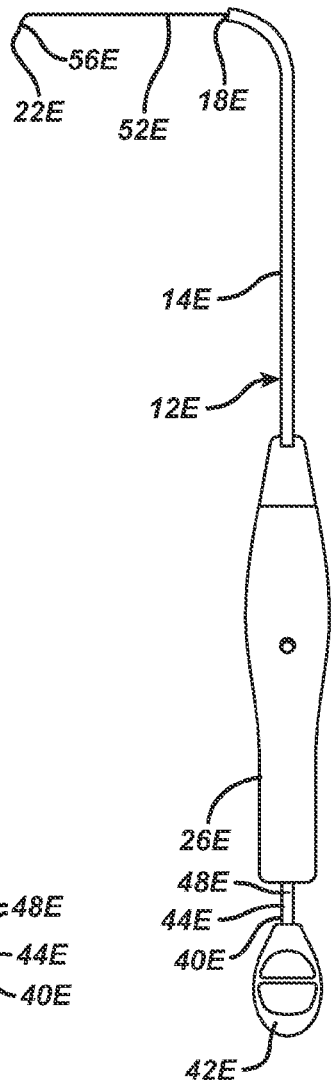

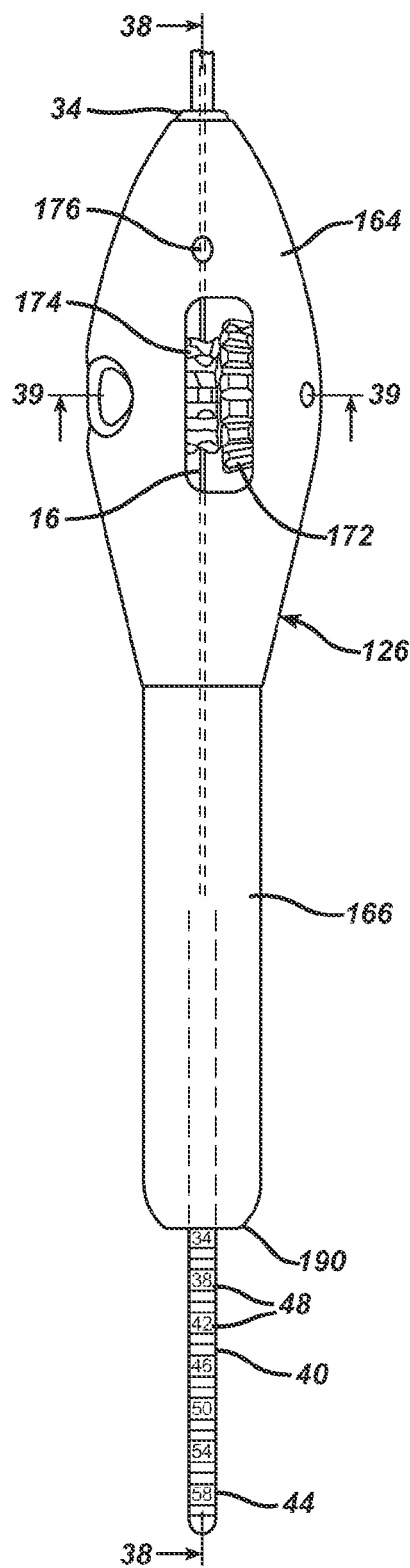
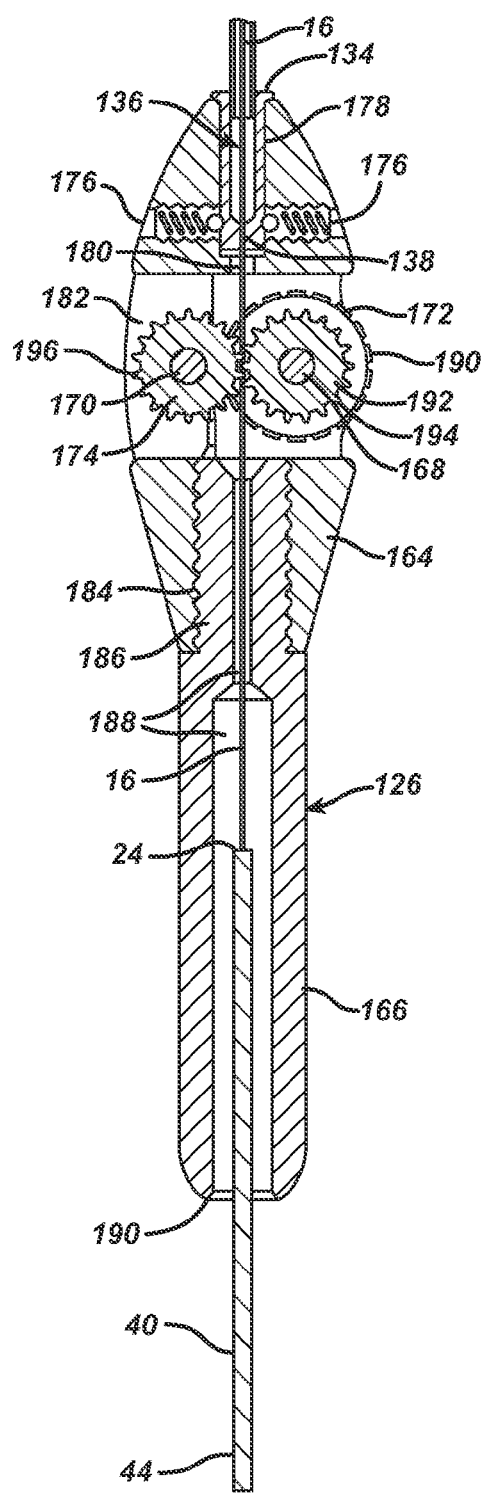

COORDINATE INSTRUMENT SET

This application is a divisional application of U.S. patent application Ser. No. 11/261,839, entitled COORDINATE INSTRUMENT SET, filed Oct. 28, 2005, which claims the benefit of U.S. Provisional Application No. 60/623,624 filed on Oct. 29, 2004, by Anthony D. Zannis, Herbert E. Schwartz, Prasanna Malaviya, Keith M. McGrath, Danny E. McAdams, Andrew M. Jacobs, Jack Farr, II and Randall L. Holcomb entitled "Coordinate Instrument Set," which is incorporated by reference herein in its entirety.

FIELD OF THE INVENTION

The present invention relates to surgical instruments and more particularly to surgical instrument sets that can be used to measure and map defects and to monitor the effects of a treatment regime over time.

BACKGROUND OF THE INVENTION

Various types of Minimally Invasive Surgery ("MIS") are being performed by surgeons, including laparoscopy, endoscopy and arthroscopy surgery. In arthroscopy, small incisions are made at the affected joint to form portals for the insertion of instruments, including a small lens and lighting system (an arthroscope). The arthroscope is connected to a viewing device, such as a television camera to allow the surgeon to see the interior of the joint. Other instruments are inserted through other portals to perform a variety of tasks. For example, the surgical instrument may include an implement for manipulating native tissue (for example, tissue grasping, tissue cutting, bone abrading), or an implement for introducing and implanting a therapeutic device.

Typical surgical instruments used in arthroscopic procedures include rongeurs, such as the Kerrison rongeur, punch forceps, basket forceps, suction punches and cup curette, for example. Examples of arthroscopic instruments are described and illustrated in O'Connor's Textbook of Arthroscopic Surgery, $2^{nd}$ ed., 1992, Chapter 19.

In many surgical settings, it is often necessary for the surgeon to make measurements between two points. Due to the confined spaces of arthroscopic surgery, measuring such distances is often quite difficult, particularly when the measurement needed is larger than the size of the incision or transverse to the direction of the incision. Arthroscopic knee surgery provides many such situations. For example, it may be helpful if a surgeon could measure the size of a defect in the meniscus of a knee, to aid in choosing the appropriate method to repair the defect.

An arthroscopic measuring device is disclosed in U.S. Pat. No. 6,427,351B1, which is incorporated by reference herein in its entirety. The device disclosed in that patent provides a handle and an extension. The extension has a distal tip for intraoperative insertion into the body through an incision. Two wires extend from a block in the handle through passageways in two separate tubes that comprise the extension. The block is connected to an actuator element. The actuator elements disclosed can be moved back and forth in a direction parallel to the longitudinal axis of the handle to move the wires out of an into the tubes. At their distal ends, the tubes diverge at a fixed angle so that the distance between the ends of the wires increases as the wires are pushed further outward and decreases as the wires are pulled back into the handle. Calibrations on the handle correspond with the distance between the ends of the wires so that the surgeon can determine one or more of the dimensions of a defect in the bone or cartilage.

Although the arthroscopic measuring device disclosed in U.S. Pat. No. 6,427,351B1 provides a useful surgical tool, operation of the actuating mechanism disclosed can be difficult for the surgeon, particularly due to friction as the wires are pushed through the divergent tube endings. In addition, use of that device may require that the surgeon use both hands to hold the handle and move the actuating mechanism. Finally, use of that device may not allow for repeatable measurements of the tissue and changes in the tissue over time.

Determining the size and location of a defect at a tissue site, such as the meniscus of the knee joint, can be useful in several arthroscopic procedures.

Common surgical procedures for treating meniscal damage include tear repairs and meniscectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Meniscectomies involve the surgical removal of part of the meniscus. Such procedures have generally been performed in cases of radial tears, horizontal tears, vertical longitudinal tears outside the vascular zone, complex tears, or defibrillation. Although meniscectomies provide immediate relief to the patient, in the long term the absence of part of the meniscus can cause cartilage wear on the condylar surface, eventually leading to arthritic conditions in the joint.

A variety of orthopaedic implants are available for treating damaged soft tissue. Orthopaedic implants for treatment of damaged menisci are disclosed in the following U.S. Pat. Nos. 6,042,610; 5,735,903; 5,681,353; 5,306,311; 5,108,438; 5,007,934; and 4,880,429.

In tear repairs, meniscectomies, and in treatments involving the use of implants, there exists a need for instruments that not only allow for measurement of the sizes of the defects, but also for mapping the defect in a repeatable manner so that the clinical results of the treatment can be monitored over time.

SUMMARY OF THE INVENTION

The present invention provides an instrument set and a surgical technique for mapping the location of a tissue defect, or the location of an implant, over time, and for measuring the defect intra-operatively.

In one aspect, the present invention provides a surgical instrument having a proximal end and a distal end. The surgical instrument comprises a tube and a ruler. The tube has a proximal end, a distal end, and an elongate channel. The ruler has a proximal end, a distal end, a straight portion received within the channel of the tube, a measurement portion between the straight portion and the distal end and an anchoring tip at the distal end. The measurement portion of the ruler includes distance indicia. The anchoring tip has a pointed end. The measurement portion of the ruler lies in a plane. The pointed end of the anchoring tip is spaced from the plane of the measurement portion of the ruler. The ruler is reciprocable in a proximal-distal direction with respect to the tube between a retracted position and an extended position.

In another aspect, the present invention provides a surgical instrument having a proximal end and a distal end. The surgical instrument comprises a tube and a ruler. The tube has a proximal end, a distal end, and an elongate channel. The ruler has a proximal end, a distal end, a straight portion received within the channel of the tube, a measurement portion between the straight portion and the distal end and a hook at the distal end. The measurement portion of the ruler includes distance indicia. The ruler is reciprocable in a proximal-distal direction with respect to the tube between a retracted position and an extended position.

In another aspect, the present invention provides a surgical instrument set comprising first and second surgical instruments. Each surgical instrument has a proximal end and a distal end, and each surgical instrument comprises a tube and a ruler. The tube of each surgical instrument has a proximal end, a distal end and a channel extending from the proximal to the distal end. The ruler of each surgical instrument has a proximal end, a distal end, a measurement portion between the proximal end and the distal end and a straight portion between the measurement portion and the proximal end. The measurement portion includes distance indicia. The straight portion of the ruler of each surgical instrument has a longitudinal axis. The ruler of each surgical instrument is reciprocable in a proximal-distal direction with respect to the tube between a retracted position and an extended position. The distal end of the ruler of the first surgical instrument comprises an anchoring tip. The anchoring tip has a pointed end. The distal end of the ruler of the second surgical instrument comprises a hook.

In another aspect, the present invention provides a surgical instrument set comprising a plurality of surgical instruments. Each surgical instrument has a proximal end and a distal end, and each surgical instrument comprises a tube and a ruler. The tube of each surgical instrument has a proximal end, a distal end and a channel extending from the proximal to the distal end. The ruler of each surgical instrument has a proximal end, a distal end, a measurement portion between the proximal end and the distal end and a straight portion between the measurement portion and the proximal end. The measurement portion includes distance indicia. The straight portion of the ruler of each surgical instrument has a longitudinal axis. The ruler of each surgical instrument is reciprocable in a proximal-distal direction with respect to the tube between a retracted position and an extended position. The measurement portion of the ruler of each surgical instrument extends in a different direction from the longitudinal axis of the straight portion when the ruler is in the extended position.

In another aspect, the present invention provides a method of mapping a feature of a tissue site of a patient with a surgical instrument. The surgical instrument includes a tube and a ruler reciprocable with respect to the tube between a retracted position and an extended position. The ruler includes a distal end and distance indicia. The method comprises moving a portion of the tube to the tissue site with at least part of the ruler retracted. The tissue is pierced with a portion of the ruler at a selected fixation point to temporarily anchor the distal end of the ruler to the tissue at the fixation point. The tube is moved with respect to the ruler so that the ruler is in the extended position. A distance is determined based on the position of the tissue feature with respect to the fixation site. The tube is moved with respect to the ruler so that the ruler is in the retracted position and the tube and ruler are removed from the tissue site.

In another aspect, the present invention comprises a method of measuring a feature of a tissue site within the body of a patient with a surgical instrument. The surgical instrument includes a tube having a proximal end and a distal end. An elongated member is reciprocable with respect to the tube between a distally retracted position and a distally extended position. The elongated member has a proximal end and a distal end, and distance indicia at its proximal end. The method comprises moving the distal end of the tube to the tissue site within the body of the patient and positioning the distal end of the elongated member at a first desired location. The tube is moved with respect to the elongated member so that the distal end of the tube is at a second desired location while the position of the distal end of the elongated member is maintained at the first desired location. The distance between the first desired location and the second desired location is determined by observing the distance indicia at the proximal end of the elongated member.

In another aspect, the present invention comprises a method of mapping a feature of a tissue site of a patient with a surgical coordinate instrument and a surgical measuring instrument. The surgical coordinate instrument includes a tube and a coordinate ruler reciprocable with respect to the tube between a retracted position and an extended position. The coordinate ruler includes a distal end and distance indicia. The surgical measuring instrument includes a tube and a ruler reciprocable with respect to the tube between a retracted position and an extended position. The ruler includes a distal end and distance indicia. The method comprises moving a portion of the tube of the coordinate instrument to the tissue site with at least part of the coordinate ruler retracted. The tissue is pierced with a portion of the coordinate ruler at a selected fixation point to temporarily anchor the distal end of the coordinate ruler to the tissue at the fixation point. The tube is moved with respect to the coordinate ruler so that the coordinate ruler is in the extended position. A portion of the tube of the measuring instrument is moved to the tissue site with at least part of the ruler retracted. The distal end of the ruler is placed at a desired location related to the tissue feature to be mapped. The tube is moved with respect to the ruler until a portion of the measuring instrument crosses the coordinate ruler. The distance between the distal end of the ruler and the coordinate ruler is then determined.

In another aspect the present invention comprises a surgical instrument having a proximal end and a distal end. The instrument comprises a handle, a tube and an elongated member. The tube extends distally from the handle, and defines a channel. A first gear is rotatably mounted to the handle, and has a plurality of grooved teeth. A second gear is rotatably mounted to the handle, and has a plurality of grooved teeth intermeshed with the grooved teeth of the first gear. The grooves of the intermeshed teeth of the first gear and second gear define a passageway aligned with the channel of the tube. The elongated member extends through the passageway and into the channel of the tube. The elongated member is movable in a proximal direction by rotating the first gear in one direction and is movable in the distal direction by rotating the first gear in the opposite direction. The elongated member has a distal end and includes distance indicia at the distal end.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 3 is a perspective view of a representative ruler assembly of one of the intra-articular measurement instruments of FIG. 1;

FIG. 4A is an enlarged side elevation of the hook at the distal end of the ruler of FIG. 3;

FIG. 4B is an enlarged bottom plan view of the hook of FIG. 4A;

FIG. 4C is an enlarged side elevation of the anchoring tip at the distal end of the ruler of the intra-articular coordinate surgical instrument of FIG. 1;

FIG. 14 is a top plan view of one of the intra-articular coordinate instruments of the set of FIG. 1, shown with the ruler in a fully retracted position;

FIG. 15 is a view similar to FIG. 14, shown with the ruler in a first intermediate extended position;

FIG. 16 is a view similar to FIGS. 14-15, shown with the ruler in a second intermediate extended position;

FIG. 17 is a view similar to FIGS. 14-16, shown with the ruler in a fully extended position;

FIG. 18 is a top plan view of one of the intra-articular measurement instruments of the set of FIG. 1, shown with the ruler in a fully retracted position;

FIG. 19 is a view similar to FIG. 18, shown with the ruler in a first intermediate extended position;

FIG. 20 is a view similar to FIGS. 18-19, shown with the ruler in a second intermediate extended position;

FIG. 21 is a view similar to FIGS. 18-20, shown with the ruler in a fully extended position;

FIG. 22 is a top plan view of another of the intra-articular measurement instruments of the set of FIG. 1, shown with the ruler in a fully retracted position;

FIG. 23 is a view similar to FIG. 22, shown with the ruler in a first intermediate extended position;

FIG. 24 is a view similar to FIGS. 22-23, shown with the ruler in a second intermediate extended position;

FIG. 25 is a view similar to FIGS. 23-24, shown with the ruler in a fully extended position;

FIG. 26 is a top plan view of another of the intra-articular measurement instruments of the set of FIG. 1, shown with the ruler in a fully retracted position;

FIG. 27 is a view similar to FIG. 26, shown with the ruler in a first intermediate extended position;

FIG. 28 is a view similar to FIGS. 26-27, shown with the ruler in a second intermediate extended position;

FIG. 29 is a view similar to FIGS. 26-28, shown with the ruler in a fully extended position;

FIG. 37 is a top plan view of an alternative handle assembly that may be used for any of the instruments illustrated in FIGS. 1 and 14-29;

FIG. 38 is a cross-section of the handle assembly of FIG. 37 taken along line 38-38 of FIG. 37;

DETAILED DESCRIPTION

Figure 1:
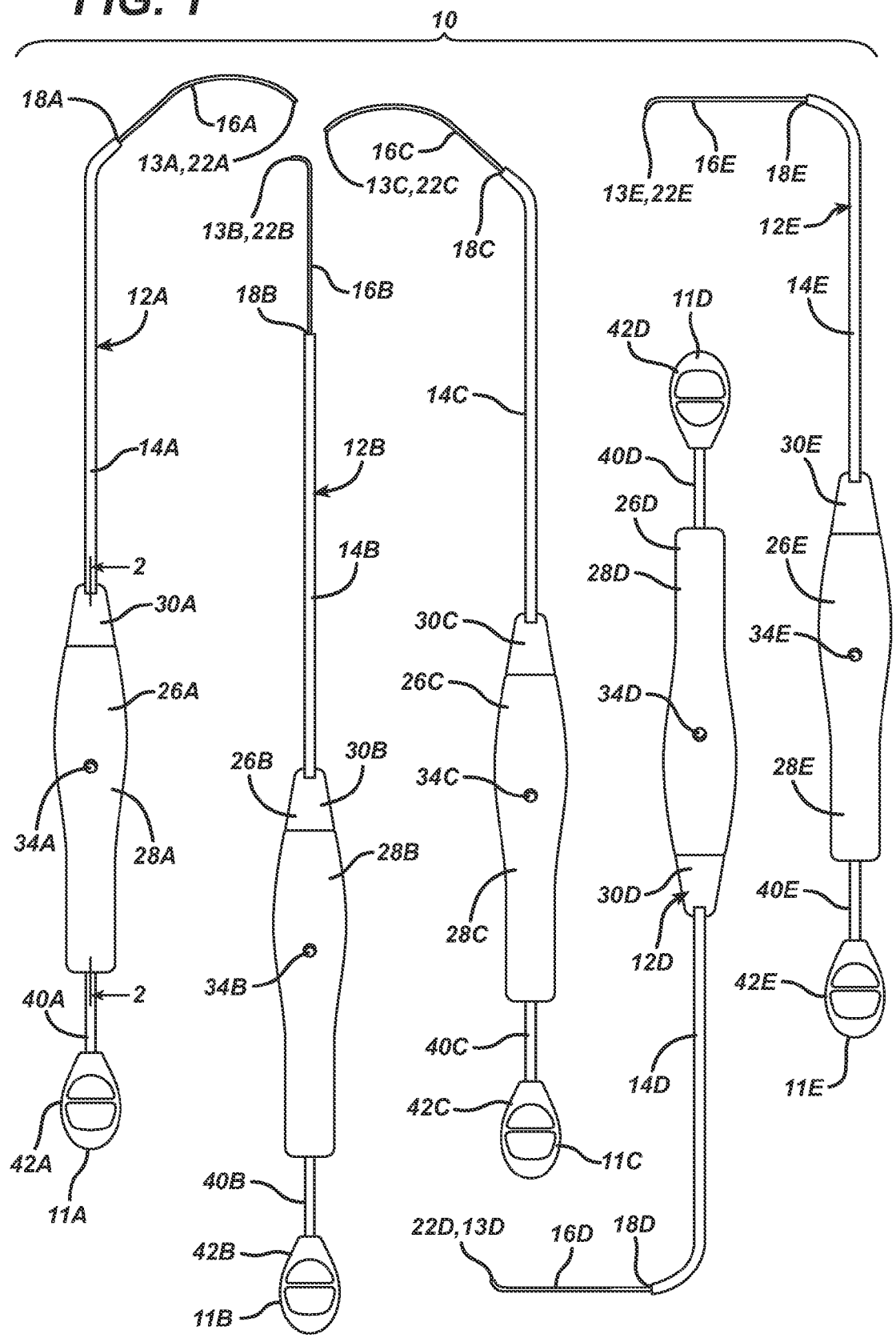
FIG. 1 is a top plan view of a set of surgical instruments with rulers in an extended position.

Surgical instruments embodying the principles of the present invention are illustrated in the accompanying drawings. FIG. 1 illustrates a surgical instrument set 10 comprising a plurality of individual intra-articular instruments 12A, 12B, 12C, 12D, and 12E that can be used to measure and map a tissue defect, such as a meniscal defect. Another intra-articular instrument that may be included in such a set is illustrated in FIGS. 22-25 at 12F. As used herein, "defect" is intended to include both tissue tears and gaps in tissue left after part of the tissue has been removed, such as through a meniscectomy. As used herein, "intra-articular instruments" refers to instruments with portions that can be received within an intra-articular space, such as the knee joint space, without significant distraction of the bones forming the joint. Although the instrument set 10 of FIG. 1 includes five individual instruments, it should be understood that the principles of the present invention are applicable to instrument sets having fewer or more than five instruments, as well as to individual instruments; the present invention should not be considered to be limited to any particular number of instruments unless expressly called for in the claims.

As shown in FIGS. 1 and 14-29, each of the illustrated instruments 12A, 12B, 12C, 12D, 12E, 12F has a proximal end 11A, 11B, 11C, 11D, 11E, 11F and a distal end 13A, 13B, 13C, 13D, 13E, 13F. As used herein, "proximal" refers to the end or portion nearer to the surgeon, and "distal" refers to the end or portion further from the surgeon.

In the instrument set 10 illustrated in FIG. 1, two of the instruments 12A and 12C comprise intra-articular coordinate instruments and the remaining instruments 12B, 12D, 12E comprise intra-articular measuring instruments. Instrument 12F also comprises an intra-articular measuring instrument. As described in more detail below, the intra-articular coordinate instruments 12A, 12C have features that allow the distal ends to be fixed to a selected anatomical site repeatedly over time, such as during surgery and post-operatively for clinical evaluation of the effectiveness of the procedure used. The intra-articular coordinate instruments 12A, 12C allow the surgeon to define a reference, baseline or benchmark that can be re-established periodically; the additional intra-articular measuring instruments 12B, 12D, 12E of the set (as well as intra-articular measuring instrument 12F) allow the surgeon to periodically establish a second reference that can be re-established periodically with respect to the position of the intra-articular coordinate instrument 12A, 12C and another anatomical reference. Two intra-articular coordinate instruments 12A, 12C are provided so that the instrument set can be used for both the medial and lateral horns of the meniscus. It should be understood that the illustrated instrument set is designed for use in treating and evaluating the meniscus; variations may be made in the illustrated instrument set for application to use at other tissue sites in the patient's body.

Figure 2:
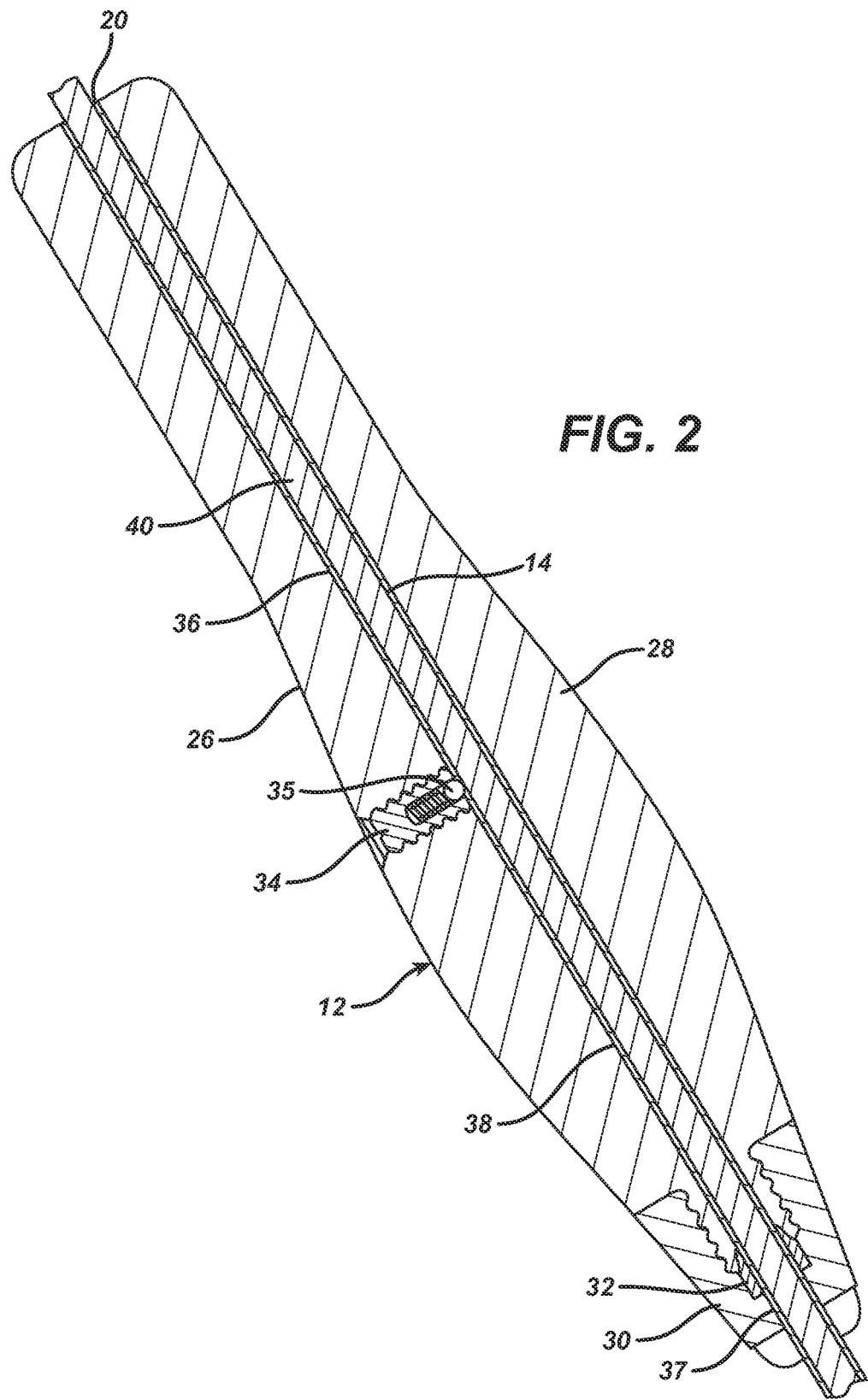
FIG. 2 is a representative longitudinal cross-section of a representative handle assembly of the instruments of FIG. 1, taken along line 2-2 of FIG. 1.

As shown in FIGS. 1 and 14-29, each illustrated instrument 12A, 12B, 12C, 12D, 12E, 12F includes a tube 14A, 14B, 14C, 14D, 14E, 14F and a ruler 16A, 16B, 16C, 16D, 16E, 16F. Each tube 14A, 14B, 14C, 14D, 14E, 14F has a distal end 18A, 18B, 18C, 18D, 18E, 18F and a proximal end. A representative proximal end of a representative tube is illustrated in FIG. 2 at 20. Each ruler 16A, 16B, 16C, 16D, 16E, 16F also has a distal end 22A, 22B, 22C, 22D, 22E, 22F and a proximal end. A representative proximal end 24B of a representative ruler 16B is illustrated in FIG. 3.

As shown in FIGS. 1 and 14-29, each illustrated instrument 12A, 12B, 12C, 12D, 12E, 12F includes a handle assembly 26A, 26B, 26C, 26D, 26E, 26F. A representative handle assembly is shown in longitudinal cross-section in FIG. 2. The description of the handle assembly of FIG. 2 is applicable to all of the handle assemblies 26A, 26B, 26C, 26D, 26E, 26F shown in FIGS. 1, 2 and 14-29. An alternative handle assembly is illustrated in FIGS. 35-38 and described below.

Each handle assembly 26A, 26B, 26C, 26D, 26E, 26F includes a main body 28A, 28B, 28C, 28D, 28E, 28F, a tapered front piece 30A, 30B, 30C, 30D, 30E, 30F a ferrule 32A (shown in FIG. 2) and a ball plunger 34A, 34B, 34C, 34D, 34E, 34F. The tapered front piece 30A, 30B, 30C, 30D, 30E, 30F includes a threaded female portion that is threaded onto a threaded male portion of the main body 28A, 28B, 28C, 28D, 28E, 28F capturing the ferrule 32A between the main body and the tapered front piece.

Figure 5:
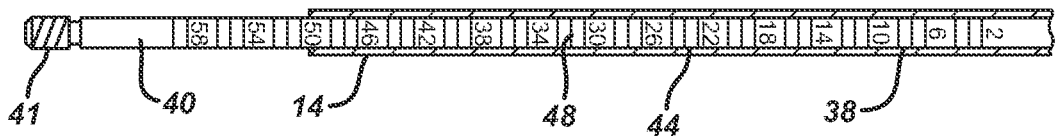
FIG. 5 is a top plan view of the proximal portion of the actuator shaft portion of a representative ruler assembly, shown with the actuator knob removed and with the actuator shaft received within the proximal portion of the tube of the surgical instrument, the tube being shown in longitudinal cross-section.
Figure 6:
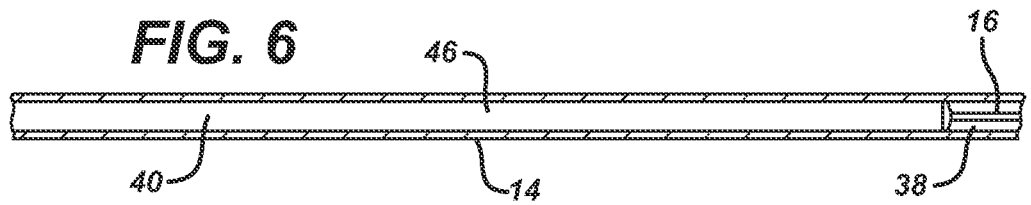
FIG. 6 is a top plan view of the distal portion of the actuator shaft of FIG. 5, illustrating the connection between the distal end of the actuator shaft and the proximal end of the ruler, with the tube being shown in longitudinal cross-section.
Figure 7:
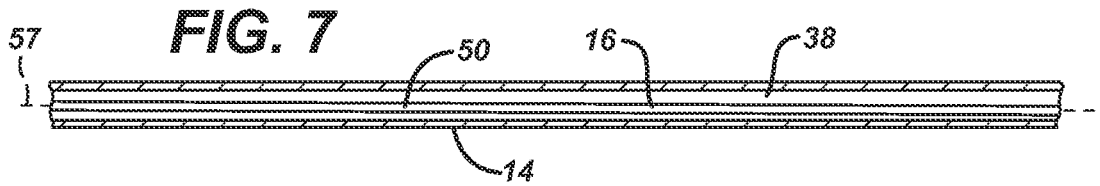
FIG. 7 is a top plan view of a representative proximal portion of the ruler adjacent to the portion illustrated in FIG. 6, with the tube being shown in longitudinal cross-section.

In FIG. 2, and in the following description of the handle assemblies, reference numbers are used without letter designations to indicate that the illustration and description applies to the handle assemblies of all the instruments 12A, 12B, 12C, 12D, 12E and 12F illustrated in FIGS. 1, 2 and 14-29. The portions of the instrument illustrated in FIGS. 5-7 are also common to all of the instruments 12A, 12B, 12C, 12D, 12E and 12F illustrated in FIGS. 1-2 and 14-29; reference numbers have also been used without letter designations in FIGS. 5-7 and in the following description to indicate that the illustrations and description applies to all of the instruments 12A, 12B, 12C, 12D, 12E, 12F.

As shown in FIG. 2, the main body 28 and tapered front piece 30 of the handle assembly have elongate central channels 36, 37 that receive a straight portion of the tube 14. As shown in FIG. 2, the tube 14 is locked in position on the handle assembly by the ball plunger 34 engaging a recess 35 in the tube 14. Also as shown in FIG. 2, the tube 14 has an elongate channel 38 that is co-axial with the elongate channels 36, 37 of the main body 28 and front piece 30.

The tube 14 receives a portion of an actuator shaft 40 in the channel 38. The proximal end of the actuator shaft 40 is threaded (as shown at 41 in FIG. 5) and is received in and connected to a threaded female opening in an actuator handle 42.

The actuator shaft 40 is reciprocable with respect to the channel 38 of the tube 14. The surgeon can move the actuator shaft 40 in the proximal-distal direction with respect to the channel by pushing and pulling on the actuator handle 42 or by holding the actuator handle 42 steady while moving the handle assembly 26 in a proximal-distal direction.

The distal end of each actuator shaft 40 has an axial female opening sized and shaped to receive the proximal end of one ruler 16 and is connected to the proximal end 24 of each ruler 16. To connect each shaft 40 to each ruler 16, any mechanical means could be used, such as a set screw, for example; alternatively or in addition, adhesive could be used, for example. The illustrated actuator shaft 40 may have an overall length of about 5.5 inches, for example, and a diameter of about 0.09 inches, for example.

A representative ruler assembly is illustrated in FIG. 3. Each ruler assembly comprises an actuator shaft 40A, 40B, 40C, 40D, 40E, a ruler 16A, 16B, 16C, 16D, 16E and an actuator handle 42A, 42B, 42C, 42D, 42E.

FIGS. 5 and 6 illustrate an exemplary actuator shaft 40 with a proximal portion 44 (shown in FIG. 5) and an integral co-axial distal portion 46 (shown in FIG. 6). The tube 14 is illustrated in cross-section. As shown in FIG. 5, the proximal portion 44 of the actuator shaft may include distance indicia, shown at 48. The distance indicia may comprise a plurality of spaced transverse markings and numerical references to indicate distance. In FIG. 6, a representative ruler is shown at 16 connected to the distal end of the actuator shaft.

Portions of a representative ruler 16 are illustrated in FIG. 7 extending longitudinally through the tube 14. The portions of the representative ruler 16 include a straight portion 50 within the tube 14.

Figure 8:
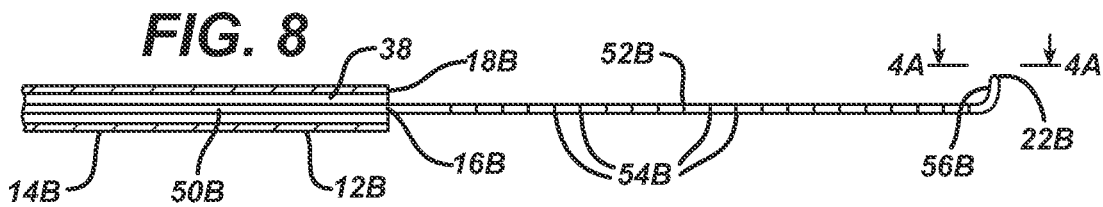
FIG. 8 is a top plan view of the distal measuring portion of the ruler wire of one of the intra-articular measurement instruments of the instrument set of FIG. 1, with the tube being shown in longitudinal cross-section.
Figure 9:
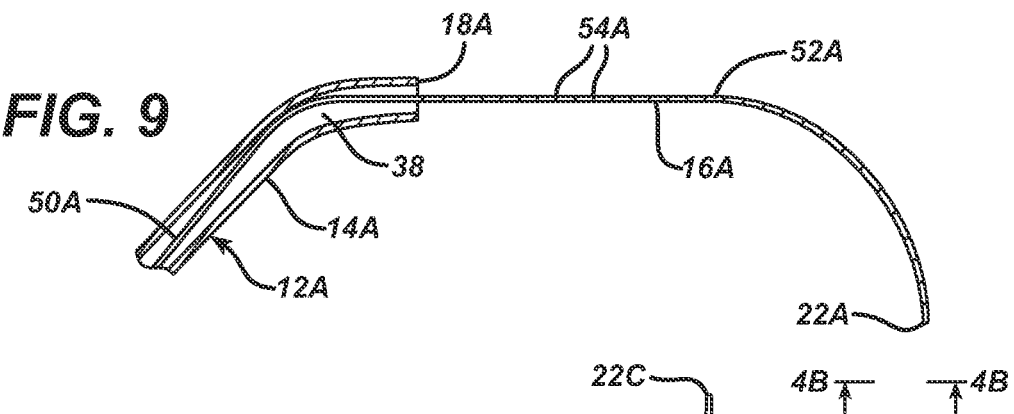
FIG. 9 is a top plan view of the distal measuring portion of the ruler of one of the intra-articular coordinate instruments of the instrument set of FIG. 1, with the tube being shown in longitudinal cross-section.
Figure 10:
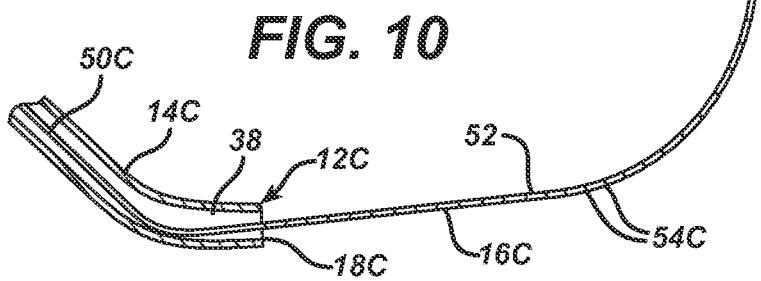
FIG. 10 is a top plan view of the distal measuring portion of the ruler of the second intra-articular coordinate instruments of the instrument set of FIG. 1, with the tube being shown in longitudinal cross-section.
Figure 11:
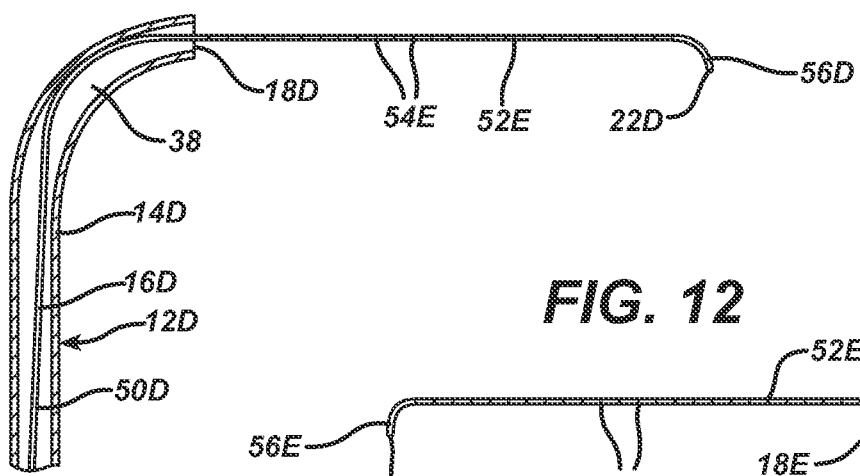
FIG. 11 is a top plan view of the distal measuring portion of the ruler of another of the intra-articular measurement instruments of the instrument set of FIG. 1, with the tube being shown in longitudinal cross-section.
Figure 12:
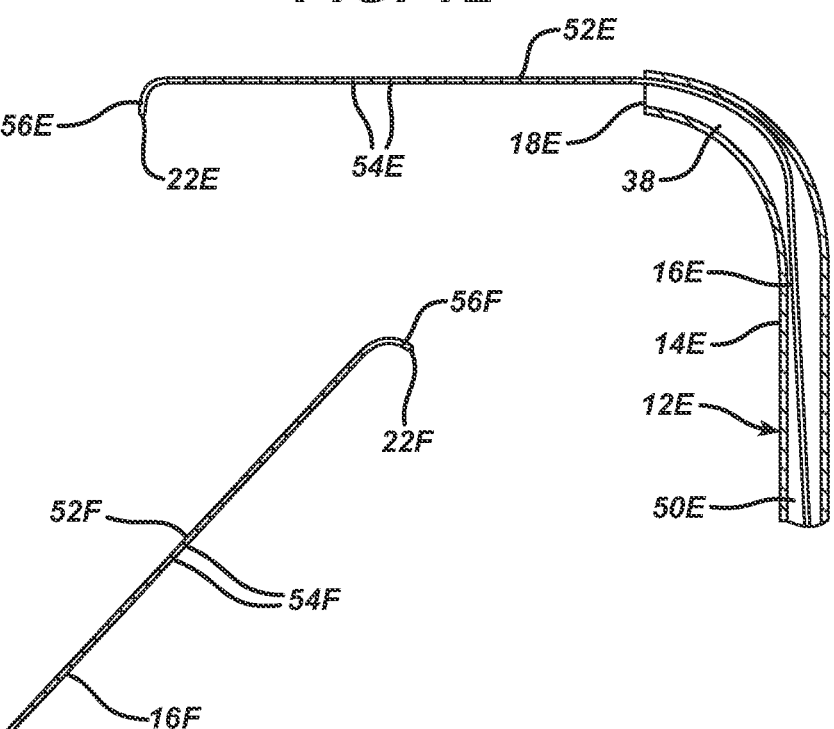
FIG. 12 is a top plan view of the distal measuring portion of the ruler of another of the intra-articular measurement instruments of the instrument set of FIG. 1, with the tube being shown in longitudinal cross-section.
Figure 13:
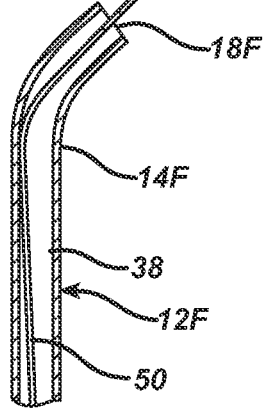
FIG. 13 is a top plan view of an alternative distal measuring portion of a ruler, with the tube being shown in longitudinal cross-section.

The distal ends of the tubes and rulers are different for each of the illustrated instruments 12A, 12B, 12C, 12D, 12E, 12F. FIG. 8 illustrates the distal ends 18B, 22B of the tube 14B and ruler 16B of the straight measuring instrument 12B. FIG. 9 illustrates the distal ends 18A, 22A of the tube 14A and ruler 16A of one of the coordinate instruments 12A with a curved distal portion and FIG. 10 illustrates the distal ends 18C, 22C of the tube 14C and ruler 16C of the other coordinate instrument 12C with a curved distal portion (the distal portion of the ruler 16C being curved in the opposite direction of the distal portion of the ruler 16A of coordinate instrument 12A). FIG. 11 illustrates the distal ends 18D, 22D of the tube 14D and ruler 16D of the measuring instrument 12D. FIG. 12 illustrates the distal ends 18E, 22E of the tube 14E and ruler 16E of the measuring instrument 12E. Another alternative configuration for a measuring instrument is shown in FIG. 13, where analogous parts are indicated by a like reference number followed by the letter designation F.

Each of the illustrated tubes 14A, 14B, 14C, 14D, 14E, 14F has an outer diameter of 0.120 inches and an inner diameter of 0.09 inches. Tubes of such diameters should be capable of being used in arthroscopic surgery, and should fit within the intra-articular space in the human knee. For use in arthroscopic surgery, it is preferred that the outer diameter of the tubes not exceed 0.47 inches (12 mm) The illustrated straight tubes 14B, 14D have overall lengths of 8.6 inches. Tubes 14A, 14C, 14F have straight portions having lengths of 8.12 inches and portions angled at 45° having lengths of 0.25 inches joined by curved portions having a radius of curvature of 0.25 inches. Tube 14E has a straight portion with a length of 7.74 inches and a curved end portion having a radius of curvature of 0.50 inches over an arc of 90°. It should be understood that these dimensions are provided as examples only; the present invention is not limited to any particular dimension or use unless expressly called for in the claims.

In each of the illustrated embodiments, the ruler 16A, 16B, 16C, 16D, 16E, 16F includes a measurement portion 52A, 52B, 52C, 52D, 52E, 52F that is integral with the straight portion 50. The integral measurement portions 52A, 52B, 52C, 52D, 52E, 52F include distance indicia 54A, 54B, 54C, 54D, 54E, 54F, comprising spaced transverse markings in the illustrated embodiments.

The illustrated rulers 16A, 16B, 16C, 16D, 16E, 16F comprise wires having diameters on the order of 0.0190-0.0195 inches and overall lengths of about 5.5 inches to 6.1 inches. It should be understood that these dimensions are provided as examples only; the present invention is not limited to any particular dimension unless expressly called for in the claims.

Referring now to the measuring instrument 12B, as shown in FIGS. 8 and 18-21, the entire tube 14B is straight from the proximal end 20B to the distal end 18B, and the measurement portion 52B of the ruler 16B is straight and co-axial with the straight portion 50 of the ruler 16B. The distal end 22B of the ruler 16B comprises a hook 56B. The hook 56B comprises a segment that curves or angles away from the straight portion, defining an angle of about 90° with the longitudinal axis 57 (shown in FIGS. 4A, 4B and FIG. 7) of the straight portion 50 while remaining co-planar therewith. As used herein, "hook" is intended to include any curved, angled or bent end portion that is sized and shaped so that it can be used to temporarily catch and hold onto tissue, and so that it can be easily removed by the surgeon. Preferably, the curved, angled or bent end has sufficient surface area so that it does not dig into the tissue, and the distal end is preferably blunt so that the end does not dig into tissue. FIG. 4B illustrates an example of a hook with a rounded distal end 22B.

The range of movement of the measuring instrument 12B is illustrated in FIGS. 18-21. FIG. 18 shows the measuring instrument 12B with the actuator shaft 40B fully retracted, thereby retracting the measurement portion 52B fully into the channel 38 of the tube 14B. The ruler may also be retracted until the hook 56B at the distal end 22B is pulled fully into the channel 38 of the tube 14B. The actuator knob or handle 42B may also be pushed or slid in the distal direction (or held steady while the handle assembly 26B is moved in the proximal direction) to extend the ruler to intermediate positions, such as those shown in FIGS. 19 and 20, and to a fully extended position, shown in FIG. 21.

Referring now to the coordinate instruments 12A and 12C, as shown in FIGS. 9-10 and 14-17, the distal portions of the illustrated tubes 14A, 14C are angled away from the straight portion at an angle of about 135°. In the coordinate instrument 12A of FIG. 9, the distal portion of the tube is angled to the right while in the coordinate instrument 12C of FIG. 10, the distal portion of the tube is angled to the left. As shown in FIGS. 9-10, the measurement portions 52A, 52C of these coordinate instruments 12A, 12C include portions that are curved; in the coordinate instrument 12A of FIG. 9, the measurement portion 52A curves to the right while in the coordinate instrument 12C of FIG. 10, the measurement portion 52C curves to the left. Each of the illustrated curved portions of the measurement portions has a radius of curvature of 0.880 inches and a 90° arc. The curvature in the illustrated coordinate instruments 12A and 12C is provided for use of the coordinate instruments in measuring and mapping portions of the meniscus, and the curvature relates to the standard curvature of the meniscus. It should be understood that the curvature can be varied, and that the shape of the measurement portion of the two coordinate instruments 12A, 12C can be varied for other anatomical sites. For example, the measurement portions 52A, 52C of the coordinate rulers 16A, 16C could be straight instead of curved. In addition, the tubes 14 could be straight along their entire lengths if desired with straight, angled or curved measurement portions of coordinate rulers.

The distal ends 22A, 22C of the coordinate instruments 12A, 12C of FIGS. 9-10 comprise anchoring tips 58A, 58C. A representative anchoring tip is illustrated in FIG. 4C; it should be understood that the following description applies to both anchoring tips.

As shown in FIG. 4C, the anchoring tip 58A includes a pointed end 60A that is spaced from the plane 62 of the straight portion 50 and measurement portion 52A of the ruler 16A. The pointed end 60A of the anchoring tip 58 is at the end of a straight segment 64A and may be razor sharp to facilitate anchoring the tip in the patient's tissue, as described below. The straight segment 64A of the anchoring tip 58A has a longitudinal axis 66A that is perpendicular to the plane 62 in the illustrated embodiment. The anchoring tip 58C of the coordinate instrument 12C of FIG. 10 has the same structure as that described above and illustrated in FIG. 4C.

FIGS. 14-17 illustrate the range of motion for the coordinate instrument 12C. FIG. 14 shows the coordinate instrument 12C with the actuator shaft 40C fully retracted, thereby retracting the measurement portion 52C fully into the channel 38 of the tube 14C. The ruler may also be retracted until the anchoring tip 58C at the distal end 22C is pulled fully into the channel 38 of the tube 14C. The actuator knob or handle 42C may also be pushed or slid in the distal direction (or held steady while the handle assembly 26C is moved in the proximal direction) to extend the ruler to intermediate positions, such as those shown in FIGS. 15 and 16, and to a fully extended position, shown in FIG. 17. As shown in FIGS. 15-17, the shape of the distal portion of the tube 14C directs the measurement portion 52C at an angle of about 135° from the longitudinal axis 57 of the straight portion of the tube 14C. Thus, as the ruler 16C is extended, it is angled to the left and curves back toward the proximal end of the coordinate instrument. As the ruler 16C is retracted, it is pulled into the tube channel 38 and flexed to fit within the confines of the tube channel 38.

It should be understood that the coordinate instrument 12A is capable of the same range of motion as that described above for the coordinate instrument 12C, although the measurement portion 52C would extend outward and to the right instead of to the left as shown in FIGS. 14-17.

Referring now to the measuring instruments 12D and 12E, as shown in FIGS. 11-12 and 26-29, the distal portions of these tubes 14D, 14E are curved away from the straight portions at an angle of about 90°. In the measuring instrument 12D of FIG. 11, the distal portion of the tube is curved to the right while in the measuring instrument 12E of FIG. 12, the distal portion of the tube is curved to the left. The distal ends of these rulers 16D, 16E include hooks 56D, 56E like those illustrated in FIGS. 4A and 4B and described above with respect to measuring instrument 12B.

The range of movement of the measuring instrument 12E is illustrated in FIGS. 26-29. FIG. 26 shows the measuring instrument 12E with the actuator shaft 40E fully retracted, thereby retracting the measurement portion 52E fully into the channel 38 of the tube 14E. The ruler 16E may also be retracted until the hook 56E at the distal end 22E is pulled fully into the channel 38 of the tube 14E. The actuator knob or handle 42E may also be pushed or slid in the distal direction (or held steady while the handle assembly 26E is moved in the proximal direction) to extend the ruler to intermediate positions, such as those shown in FIGS. 27 and 28, and to a fully extended position, shown in FIG. 29.

If a ruler with a straight measurement portion was used with the tube 14A, 14C with the angled distal portions instead of a ruler with a curved portion, the movement of the measurement portion would be like that shown in the alternative embodiment 12F of FIGS. 22-25. It should be understood that an instrument set 10 may also include instruments like that shown in FIGS. 22-25, as well as those where the distal end of the tube angles to the right instead of to the left.

As shown in FIGS. 12 and 27-29, the shape of the distal portion of the tube 14E directs the measurement portion 52E at an angle of about 90° from the longitudinal axis 57 of the straight portion of the tube 14E. Thus, as the ruler 16E is extended, it is angled to the left of the measuring instrument. As the ruler 16E is retracted, it is pulled into the tube channel 38 and flexed to fit within the confines of the tube channel 38.

It should be understood that the measuring instrument 12D is capable of the same range of motion as that described above for the measuring instrument 12E, although the measurement portion 52D would extend outward and to the right instead of to the left as shown in FIGS. 27-29.

All of the above-described designs for the tubes 14A, 14B, 14C, 14D, 14E, 14F, actuators 40A, 40B, 40C, 40D, 40E, 40F and rulers 16A, 16B, 16C, 16D, 16E, 16F can be used with the alternative handle assembly 126 illustrated in FIGS. 37-38. In FIGS. 37-40 and in the following description of the alternative handle assembly, reference numbers are used without letter designations to indicate that the handle assembly can be used with any of the tubes 14A-14F, rulers 16A-16F and actuators 40A-40F illustrated or described herein.

As shown in FIGS. 37-38, the handle assembly 126 includes a base 164, a handle post 166, two screws 168, 170, a thumb gear assembly 172, a spur gear 174 and two ball plungers 176. The base 164 has a distal longitudinal channel 178 (shown in FIG. 38) and two transverse bores in communication with the distal longitudinal channel. The distal longitudinal channel 178 receives a shoulder 134 that has two dimples. The shoulder 134 receives the distal end 18 of a tube 16; the tube and shoulder are connected in any suitable manner, such as by welding. The assembly of the tube 16 and shoulder 134 is held in place at the distal end of the base 164 by the two ball plungers 176, which engage the dimples in the shoulder 134.

The distal longitudinal channel 178 communicates with a longitudinal distal bore 180, which communicates with a central open area 182 in the base 164, which communicates with a longitudinal female threaded opening 184. The female threaded opening 184 receives a distal male threaded portion 186 (see FIG. 38) of the post 166. The post 166 includes a longitudinal channel 188 that communicates with the central open area 182 and extends to the proximal end 190 of the post 166. The distal longitudinal channel 178 and longitudinal distal bore 180 of the base 164 and longitudinal channel 188 of the post 166 are co-axial with the channel 38 of the tube 14.

The ruler 16 extends through the channel 38 of the tube 14, through the distal channel 136 of the shoulder 134, through the reduced diameter proximal channel 138 of the shoulder 134, through the longitudinal distal bore 180 of the base 164, through the central open area 182 of the base 164 and through the longitudinal channel 188 of the post 166. In the central open area 182 of the base 164, the ruler 16 passes between part of the thumb gear assembly 172 and the spur gear 174.

Figure 39:
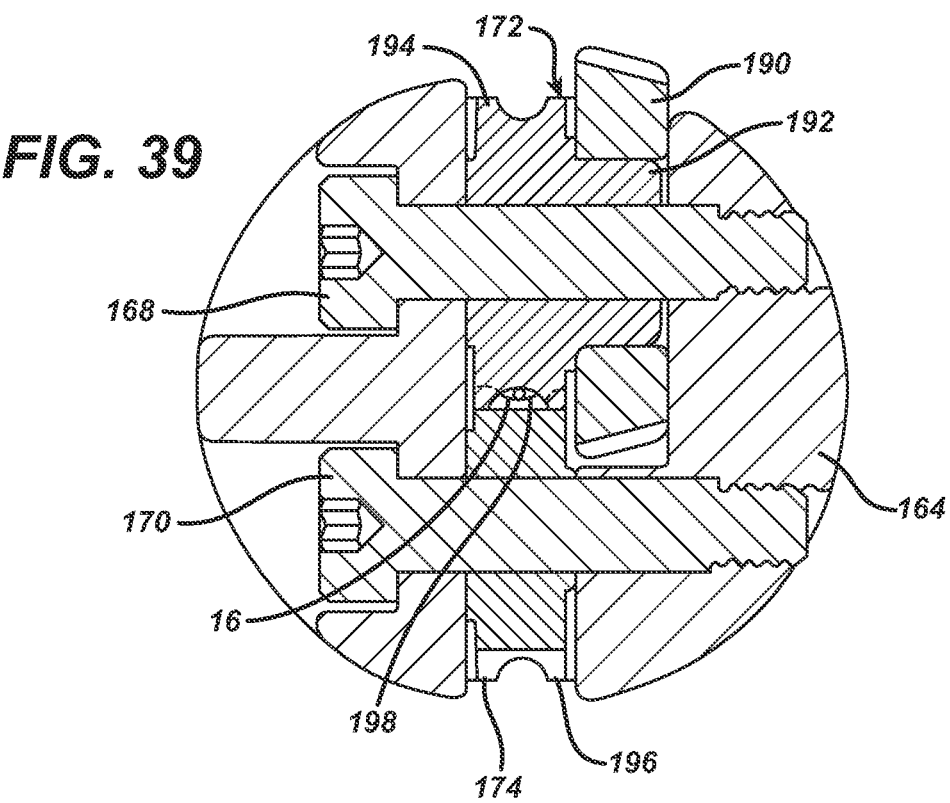
FIG. 39 is a cross-section of the handle assembly of FIG. 37 taken along line 39-39 of FIG. 37.
Figure 40:
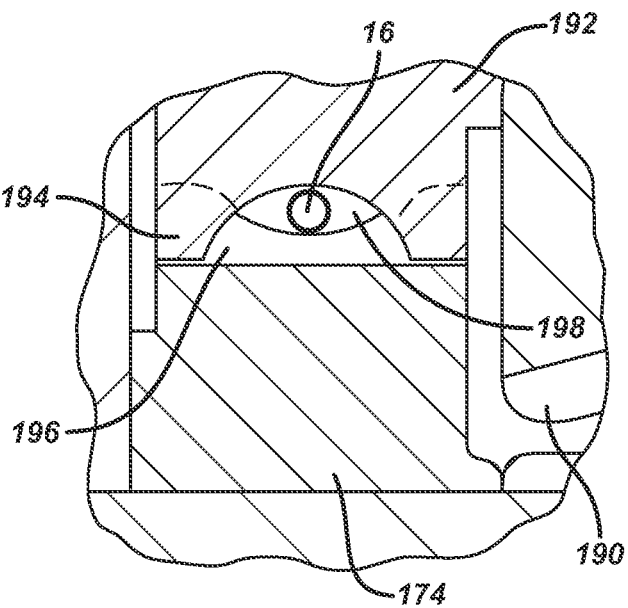
FIG. 40 is an enlarged view of the cross-section of FIG. 39.

As shown in FIGS. 39 and 40, the thumb gear assembly 172 is mounted to the base 164 by the screw 168 and the spur gear 174 is mounted to the base 164 by the screw 170. The thumb gear assembly 172 is freely rotatable on the smooth shaft of the screw 168 and the spur gear 174 is freely rotatable on the smooth shaft of the screw 170.

The thumb screw assembly 172 comprises a thumb wheel 190 and a thumb gear 192 mounted coaxially on the screw 168. The outer surface of the thumb wheel 190 has a plurality of axial splines so that the surgeon can easily rotate the wheel 190 with a thumb or finger. The thumb wheel 190 receives a reduced diameter portion of the thumb gear 192 so that the thumb wheel 190 and thumb gear 192 rotate together.

The thumb gear 192 has a plurality of grooved teeth 194 that intermesh with the grooved teeth 196 of the spur gear 174. As shown in FIG. 40, the intermeshing grooved teeth 194 of the thumb gear 192 and grooved teeth 196 of the spur gear 174 define a passageway 198 that is co-axially aligned with the distal longitudinal channel 178 and longitudinal distal bore 180 of the base 164 and longitudinal channel 188 of the post 166. A portion of the ruler 16 extends between the thumb gear 192 and the spur gear 174, passing through the passageway 198 defined by the grooved teeth 194, 196. Where the proximal surface of one of the thumb gear teeth 194 meets and engages the distal surface of one of the spur gear teeth 196, at least one of the transverse dimensions of the passageway 198 is slightly less than the outer diameter of the ruler 16 so that the intermeshing teeth 194, 196 grip the ruler 16. Thus, the ruler 16 can be reciprocated in the proximal-distal direction by rotating the thumb wheel 190, and the surgeon can extend and retract the measurement portion 52 of the ruler 16 with the same hand used to grasp the handle post 166. As shown in FIG. 38, the proximal end 24 of the ruler 16 is connected to the shaft 40 within the longitudinal channel 188 of the post 166. Shaft 40 includes distance indicia 48 as in the prior embodiments, and extension of the measurement portion 52 of the ruler 16 causes a corresponding retraction of the shaft 40 through an opening in the post 166 of the handle assembly 126 into the longitudinal channel 188 of the post 166.

To allow the rulers 16A, 16B, 16C, 16D, 16E, 16F to be retracted and extended through the illustrated ranges of motions, the rulers may be made of a shape-memory material or of a super-elastic material. The ruler material should be one that can be shaped into a pre-determined shape (such as straight, angled or curved or a combination of straight, angled or curved segments), marked with distance indicia, have sufficient rigidity to retain its pre-determined shape when extended over a distance such as 10-50 mm, that can deform to fit within the shape of the channel 38 of the tube 14 when retracted, that can be directed in a particular direction by the shape of the channel when extended, and that will regain its pre-determined shape when extended beyond the channel. Finally, the material should be one that is suitable for surgical use. An example of a suitable material is nitinol (nickel-titanium alloy). It is anticipated that other alloys and other materials such as polymers and composites will also be usable as a shape memory or super-elastic material for the rulers. Accordingly, the present invention should not be limited to any particular material unless expressly called for in the claims.

The rulers 16A, 16B, 16C, 16D, 16E, 16F can be pre-formed into the desired shape, such as the curved shape of rulers 16A, 16C or the straight shape of rulers 16B, 16D, 16E, 16F. The hooks 56 can be pre-formed in at the distal ends of the rulers 16B, 16C, 16D, 16E, 16F (and the distal ends rounded or otherwise made blunt) and distal segments can be bent and sharpened to form the sharp anchoring tips 58A, 58C of the coordinate rulers 16A, 16C.

All of the other components of the surgical coordinate and measuring instruments 12A, 12B, 12C, 12D, 12E, 12F can be made of standard materials for surgical instruments. For example, the main body 28A, 28B, 28C, 28D, 28E, 28F, front piece 30A, 30B, 30C, 30D, 30E, 30F and ferrule 32A of the handle assembly 26A, 26B, 26C, 26D, 26E, 26F can be made of acetyl co-polymer, as can the actuator handle 42A, 42B, 42C, 42D, 42E, 42F. The actuator shaft 40A, 40B, 40C, 40D, 40E, 40F can be made of 304 stainless steel bar. All of the components of the handle assembly 126 of FIGS. 37-38 can also be made of standard materials for surgical instruments. For example, the base 164 and post 166 can be made of acetyl co-polymer, and the gears 174, 192, thumb wheel 190, screws 168, 170 and ball plungers 176 can be made of stainless steel. It should be understood that all of these materials are identified as examples only; the present invention is not limited to any particular material unless expressly called for in the claims.

Use of the illustrated instruments is described below and illustrated in FIGS. 30-33 in treating a defect in the meniscus, shown at 70 in FIGS. 30-33. In the illustrations, the tissue defect 72 comprises a gap in the posterior portion of the medial horn 74 of the meniscus 70 created by a partial meniscectomy. Although not described in detail below, it should be understood that the technique described below can also be used in treating tissue defects in other areas of the medial horn 74 of the meniscus as well as in the lateral horn 76 of the meniscus. It should also be understood that the technique described below can also be applied in treating defects at other tissue sites in a patient's body. In FIGS. 30-33, a portion of the anterior cruciate ligament is shown at 78 and a portion of the posterior cruciate ligament is shown at 80.

Figure 30:
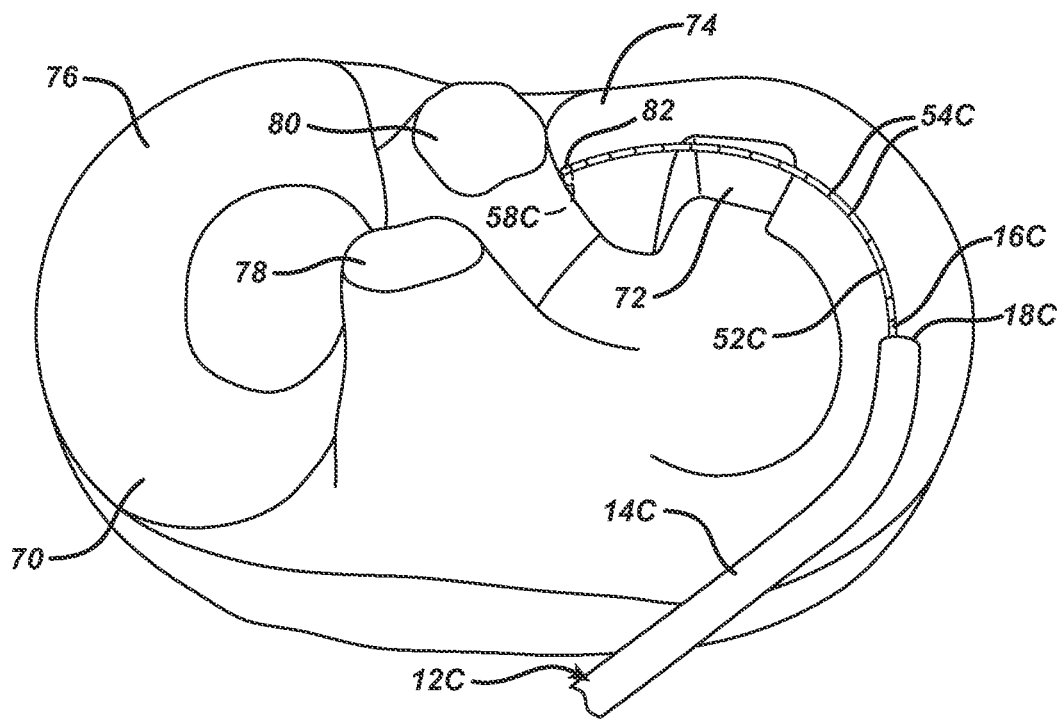
FIG. 30 is a diagrammatic perspective view of a meniscus shown with one of the intra-articular coordinate instruments of the set of FIG. 1 anchored at a fixation point.
Figure 31:
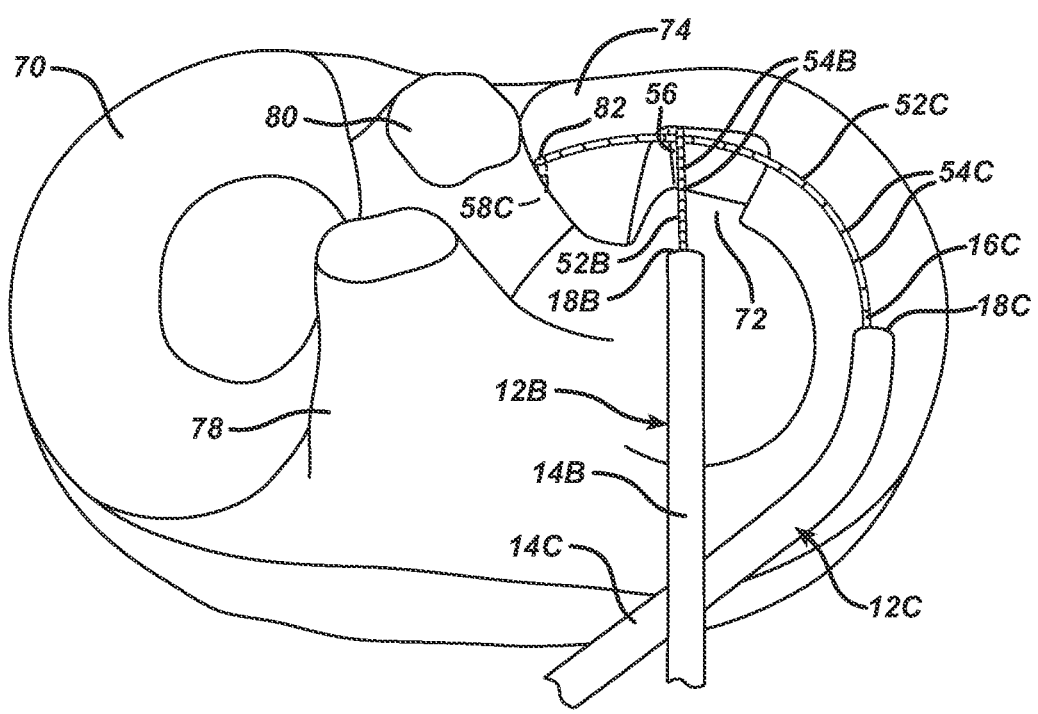
FIG. 31 is a view similar to FIG. 30, shown with the intra-articular coordinate instruments of the set of FIG. 1 anchored at a fixation point and one of the intra-articular measuring instruments of the set of FIG. 1 crossing the intra-articular coordinate instrument.
Figure 32:
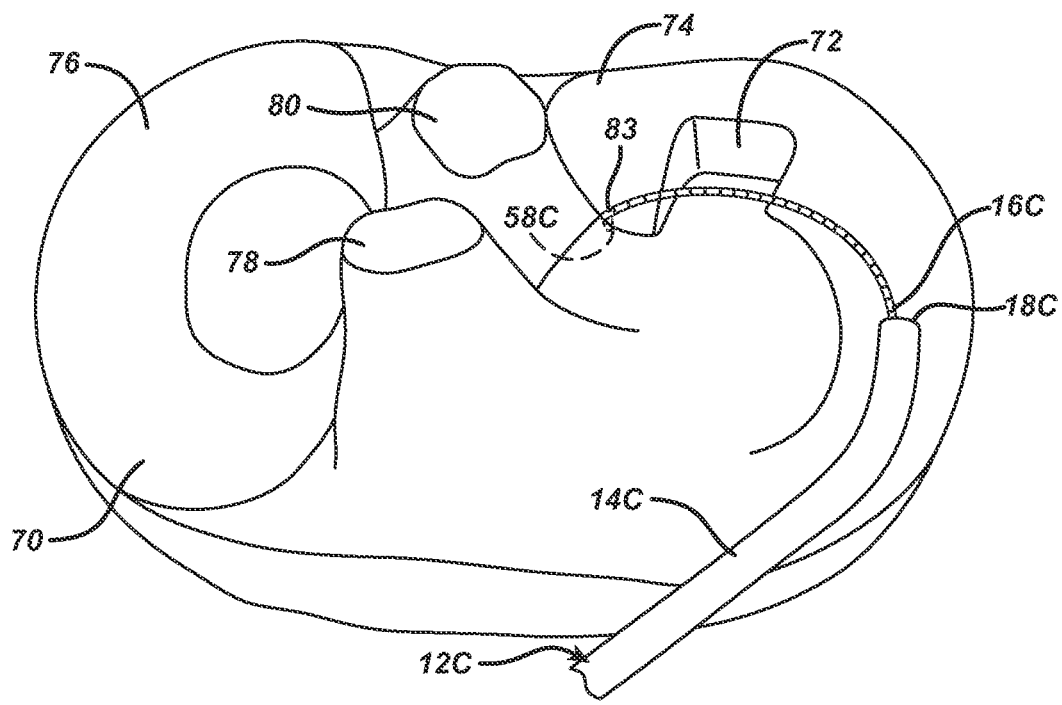
FIG. 32 is a diagrammatic perspective view of a meniscus shown with one of the intra-articular coordinate instruments of the set of FIG. 1 anchored at an alternative fixation point.
Figure 33:
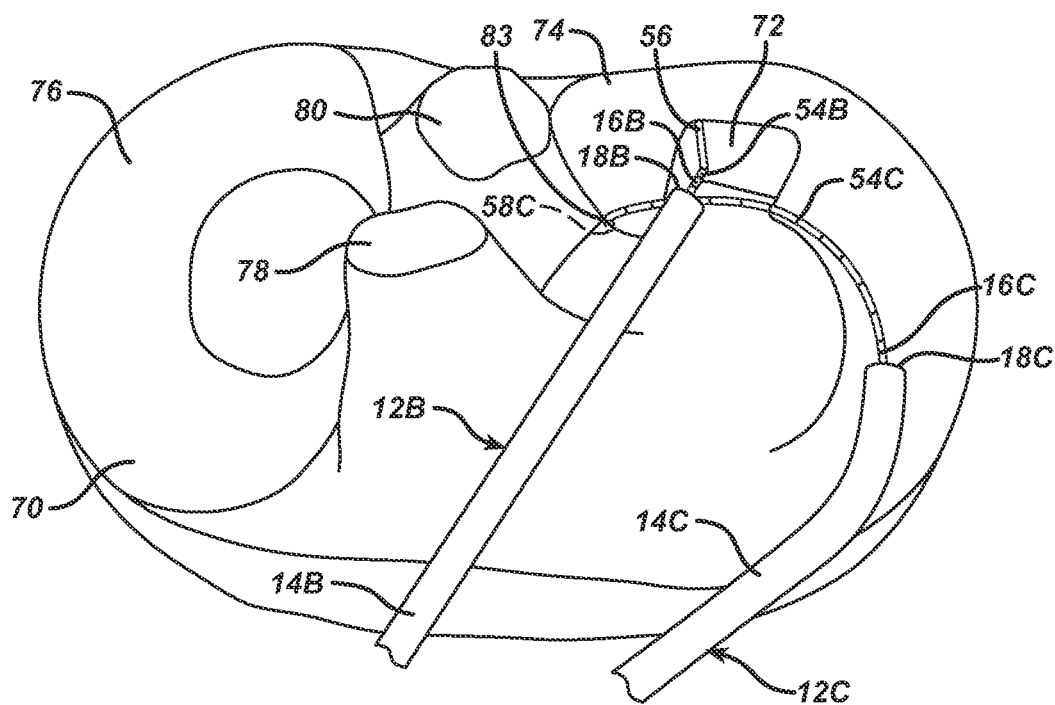
FIG. 33 is a view similar to FIG. 32, shown with the intra-articular coordinate instruments of the set of FIG. 1 anchored at the alternative fixation point of FIG. 32 and one of the intra-articular measuring instruments of the set of FIG. 1 crossing the intra-articular coordinate instrument.

The surgeon can perform standard arthroscopic procedures to create portals to gain access to the medial horn 74 of the meniscus. Standard cannulae can be inserted through the portals, and a standard arthroscope (not shown) can be used for visualization of the tissue site. The appropriate coordinate instrument (12C for example) is selected and the measurement portion 52C of the coordinate ruler 16C is fully retracted into the channel 38 of the tube 14C (as shown in FIG. 14). The tube 14C may then be inserted through one of the cannulae and guided to the medial meniscus 74. When the distal end 18C of the tube 14C is in position at the medial meniscus 74, the surgeon can fix the anchor 58C at a pre-selected anatomical site by pressing the sharp pointed end 60 of the anchor 58C into the tissue. In FIGS. 30-31, the anchor 58C is fixed in the posterior horn of the medial meniscus 74 at its juncture with the posterior cruciate ligament 80, midway between the anterior and posterior edge of the meniscus. This fixation point, designated 82 in FIGS. 30 and 31, then serves as a first benchmark for mapping the location of the defect 72. In FIGS. 32-33, the anchor 58C is fixed in the anterior portion of the posterior horn of the medial meniscus 74 at its juncture with the posterior cruciate ligament 80; this alternate fixation point is designated 83 in FIGS. 32-33.

With the anchor 58C secured to the meniscus, the surgeon can then gently pull the handle assembly 26C in the proximal direction with one hand while holding onto the actuator handle 42C with the other hand. As the surgeon does so, the measurement portion 52C of the coordinate ruler 16C is extended out of the channel 38 of the tube 14C and the proximal portion 44C of the actuator shaft 40C is drawn into the channel 38 at the proximal end of the tube 14C. The surgeon may stop pulling when the distal end 18C of the tube 14C reaches an anatomical feature or defect feature, such as the first edge of the defect 72, and note the distance from the fixation point 82 or 83 by observing the distance indicia 48C on the proximal portion 44C of the actuator shaft 40C or by observing the distance indicia 54C on the measurement portion 52C of the ruler 16C through the arthroscope. The surgeon may then continue pulling the handle assembly 26C until the distal end 18C of the tube 14C reaches another anatomical feature or defect feature, such as the opposite edge of the defect 72, and note the distance from the fixation point 82 or 83 by observing the distance indicia 48C on the proximal portion 44C of the actuator shaft 40C or by observing the distance indicia 54C on the measurement portion 52C of the ruler 16C through the arthroscope. Thus, the surgeon can map two edges of the defect 72 with respect to a fixed reference 82 or 83 and concurrently measure the distance between two edges of the defect 72.

Although the surgeon may choose to use the coordinate instruments 12A, 12C for all distance measurements, the surgeon may advantageously use the measuring instruments 12B, 12D, 12E, 12F in combination with the coordinate instrument 12A or 12C to continue mapping the location of the defect. In addition, the surgeon could use one or more of the measuring instruments 12B, 12D, 12E, 12F without using one of the coordinate instruments 12A, 12C if desired.

Depending on the surgeon's desired approach, one of the measuring instruments 12B, 12D, 12E, 12F may be selected. In FIGS. 31 and 33, the measuring instrument 12B with the straight tube 14B is illustrated being used. Further mapping with the measuring instrument 12B may be done with the coordinate instrument 12C fixed in place so that measurements can be taken with reference to the fixed distance indicia 54C of the coordinate instrument 12C. These fixed distance indicia 54C may serve as additional benchmarks, or may be used to define a baseline, for further measurements for mapping.

The measurement portion 52B of the ruler 16B is fully retracted into the channel 38 of the tube 14B (as shown in FIG. 18). The tube 14B may then be inserted through one of the cannulae and guided to the medial meniscus 74. When the distal end 18B of the tube 14C is in position at the medial meniscus 74, the surgeon can place the hook 56 at the distal end 22B of the measurement portion 52B of the ruler 16B along the measurement portion 52C of the coordinate ruler 16C as shown in FIG. 31, or at an anatomical feature, such as the posterior surface of the defect 72 as shown in FIG. 33. The surgeon may then gently pull the handle assembly 26B in the proximal direction with one hand while holding onto the actuator handle 42B with the other hand. As the surgeon does so, the measurement portion 52B of the ruler 16B is extended out of the channel 38 of the tube 14B and the proximal portion 44B of the actuator shaft 40B is drawn into the channel 38 at the proximal end of the tube 14B. As shown in FIG. 31, the surgeon may stop pulling when the distal end 18B of the tube 14B reaches an anatomical feature or defect feature (such as the interior edge of the defect 72; alternatively, as shown in FIG. 33, the surgeon may stop pulling when the distal end 18B of the tube 14B reaches a selected indicia on the coordinate ruler 52C serving as a benchmark. Since the length of the exposed measurement portion 52B of the ruler 16B corresponds with the length of the actuator shaft 40B drawn into the tube 14B, the surgeon may note the distance indicia shown at the juncture of the exposed actuator shaft 40B and the proximal end of the handle assembly 26B (see, for example, FIG. 36); the distance indicia shown at this juncture (shown at 49 in FIG. 36) corresponds with the distance between a selected distance indicia on the coordinate ruler 16C and the hook 56 (and thereby the distance to the anatomical or defect feature on or against which the hook rests). Alternatively, the surgeon can observe the distance indicia 54B on the measurement portion 52B of the ruler 16B through the arthroscope. The surgeon may then continue this process to map the location of selected portions of the defect 72 with respect to the location of selected points along the measurement portion 54C of the coordinate ruler 16C Essentially, the surgeon can map the defect with respect to benchmarks provided by selected distance indicia (or a baseline defined by the selected distance indicia) on the measurement portion 54C of the coordinate ruler 16C. If desired, the surgeon can also measure the position of several points along the measurement portion 54C of the coordinate ruler 16C with respect to fixed anatomical reference positions to ensure that placement of the measurement portion 54C of the coordinate ruler 16C is consistent in future uses of the instrument set.

Figure 34:
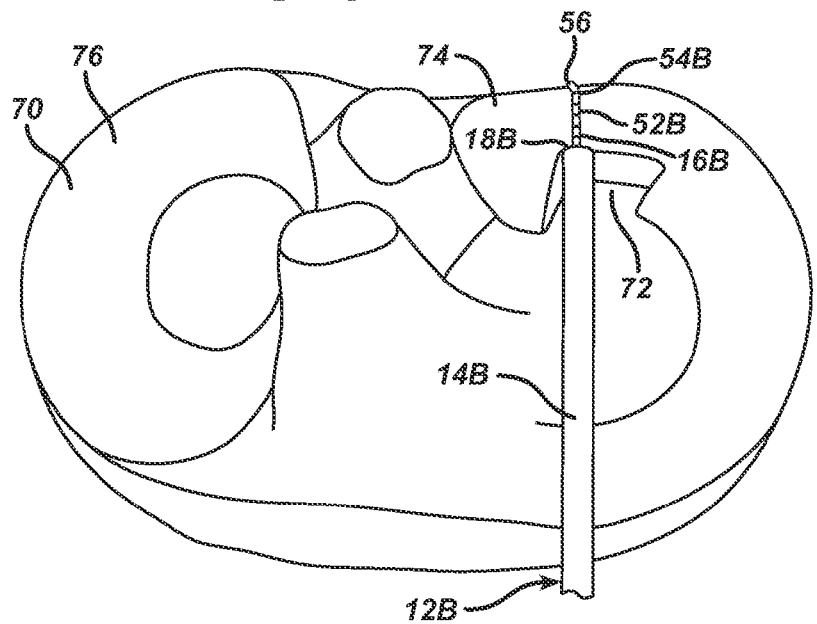
FIG. 34 is a diagrammatic representation of a meniscus with one of the intra-articular measuring instruments of the set of FIG. 1 shown without any intra-articular coordinate instrument.
Figure 36:
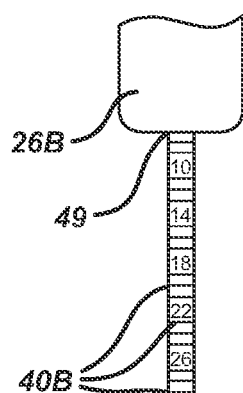
FIG. 36 is a top plan view of the distal portion of the actuator used in the measurements illustrated in FIG. 34 or 35.
Figure 35:
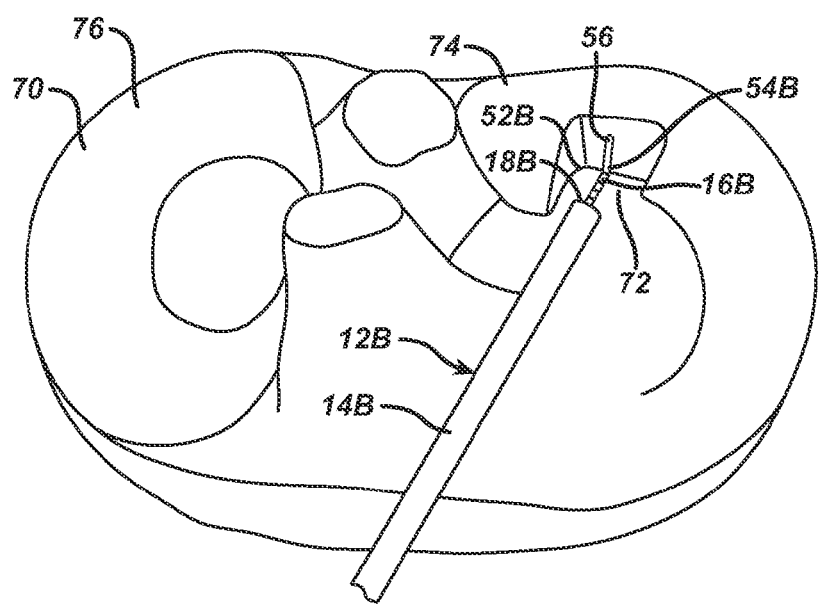
FIG. 35 is a diagrammatic representation of a meniscus with one of the intra-articular measuring instruments of the set of FIG. 1 shown without any intra-articular coordinate instrument.

Measurements can also be taken using one of the intra-articular measuring instruments 12B, 12D, 12E, 12F without using the intra-articular coordinate instrument 12A or 12C. FIGS. 34 and 35 illustrate use of measuring instrument 12B, but it should be understood that the following method may be used with any of the intra-articular measuring instruments 12B, 12D, 12E, 12F. As described above, the measurement portion 52B of the ruler 16B is first fully retracted into the channel 38 of the tube 14B (as shown in FIG. 18). The tube 14B is then inserted through one of the cannulae and guided to the desired site, such as the medial meniscus 74. When the distal end 18B of the tube 14C is in position in the joint space, the surgeon may place the hook 56 at the distal end 22B of the measurement portion 52B of the ruler 16B to an anatomical or defect feature: in FIG. 34, the hook 56 is illustrated placed along the posterior edge of the meniscus, with the hook 56 facing down (distally); in FIG. 35, the hook is illustrated placed against the posterior surface of the defect 72, with the hook 56 facing upward (proximally). The surgeon may then gently pull the handle assembly in the proximal direction with one hand while holding onto the actuator handle 42B with the other hand. As the surgeon does so, the measurement portion 52B of the ruler 16B is extended out of the channel 38 of the tube 14B and the proximal portion 44B of the actuator shaft 40B is retracted into the channel 38 at the proximal end of the tube 14B. The surgeon may stop pulling when the distal end 18B of the tube 14B reaches another anatomical or defect feature, such as the top edge of the defect 72 as illustrated in FIG. 34 or the interior edge of the defect 72 as illustrated in FIG. 35, for example. The surgeon may then note the distance by observing the distance indicia 54B on the measurement portion 52B of the ruler 16B through the arthroscope; alternatively, since the length of the measurement portion 52B of the ruler 16B exposed beyond the distal end 18B of the tube 14B corresponds with the length of the actuator 40B withdrawn into the handle assembly 26B, the surgeon can also observe the distance indicia 49 on the actuator shaft 40B, as illustrated in FIG. 36. The surgeon can repeat these steps at additional locations to complete the measurement of the defect 72 or other anatomical feature.

If the handle assembly 126 of FIGS. 37-38 is used, the surgeon can move the coordinate rulers 16A, 16C and measurement rulers 16B, 16D, 16E, 16F throughout their ranges of motion with the same hand used to hold the handle assembly 126, simply by rotating the thumb wheel 190. Thus, the surgeon will have a free hand for performing other tasks if desired.

The surgeon can use the measurements taken with the instrument set 10 to determine the appropriate size of implant to be used in treating the defect 72 and can then deliver the appropriate implant to the site and fix the implant in place. An example of an implant that may be used in repairing a meniscal defect is disclosed in U.S. patent application Ser. No. 10/747,349 entitled "Implantable Tissue Repair Device and Method," filed on Dec. 29, 2003 by Jenks, Malaviya, Schwartz, Whalen and Zannis, which is incorporated by reference herein in its entirety. The implant may include a cover and a wedge as disclosed therein, and the cover may extend beyond the sides or edges of the wedge to provide fixation areas that may be used to suture or otherwise fix the implant to native tissue or bone, with the wedge generally filling the gap in the native meniscal tissue left after a partial meniscectomy. It is anticipated that surgeons will trim the fixation areas of the implant intra-operatively to suit the needs of the individual patient. The therapeutic implant, method of making the implant, and method of repairing cartilage using the implant may include the teachings of the following United States Patent Applications, the complete disclosures of which are incorporated by reference herein: Ser. No. 10/172,347 entitled "Hybrid Biologic-Synthetic Bioabsorbable Scaffolds" (U.S. Patent Publication No. 20030023316A1); Ser. No. 10/195,334 entitled "Cartilage Repair and Regeneration Scaffolds and Method" (U.S. Patent Publication No. 20030033021A1); Ser. No. 10/195,341 entitled "Hybrid Biologic/Synthetic Porous Extracellular Matrix Scaffolds" (U.S. Patent Publication No. 20030021827A1); Ser. No. 10/195,344 entitled "Unitary Surgical Device and Method" (U.S. Patent Publication No. 20030078617A1); Ser. No. 10/195,354 entitled "Porous Extracellular Matrix Scaffold and Method" (U.S. Patent Publication No. 20030044444A1); Ser. No. 10/195,606 entitled "Cartilage Repair and Regeneration Device and Method" (U.S. Patent Publication No. 20030033022A1); Ser. No. 10/195,633 entitled "Porous Delivery Scaffold and Method" (U.S. Patent Publication No. 2003-0049299A1); Ser. No. 10/195,719 entitled "Devices from Naturally Occurring Biologically Derived Materials" (U.S. Patent Publication No. 20030032961A1); and Ser. No. 10/195,794 entitled "Meniscus Regeneration Device and Method" (U.S. Patent Publication No. 20030036797A1). It should be understood that the particular implants, features of the implants, methods of making the implants and methods of repairing cartilage are provided as examples only; the present invention is not limited to the illustrated implants or to meniscal implants or to any particular method of making or using implants unless expressly called for in the claims.

To confirm that an appropriate size of implant is selected, the templates disclosed in the United States Provisional Patent Application entitled "Implant System and Method With Sizing Templates," filed concurrently herewith by Anthony Zannis, Danny E. McAdams, Brian A. Magee, Herbert E. Schwartz and Andrew M. Jacobs (and which is incorporated by reference herein in its entirety) may be used. To deliver the implant arthroscopically, devices may be used like those disclosed in the following United States Patent Applications, which are incorporated by reference herein in their entireties: U.S. patent application Ser. No. 10/610,287 entitled "Slide and Kit for Delivering Implants" (filed Jun. 30, 2003) and U.S. Provisional Patent Application Ser. No. 60/483,804 entitled "Instrument for Delivery of Implant" (filed Jun. 30, 2003). However, the present invention is not limited to any particular implant, surgical technique or surgical instrument unless expressly set forth in the claims.

To evaluate the effectiveness of the treatment, the surgeon can repeat the steps outlined above at different intervals during the healing process. For example, at six months following implantation, the surgeon can once again create arthroscopic portals and insert cannulae to gain access to the tissue site. The appropriate intra-articular coordinate instrument 12A, 12C is selected and introduced as described above. The pointed anchor tip 58C is fixed at the same anatomical reference 82 as in the initial surgery and the measurement portion 52C is extended as described above. A measuring instrument 12B, 12D, 12E, 12F with a hook 56 at the distal end of the ruler 16B, 16D, 16E, 16F can then also be introduced to the tissue site as discussed above. The surgeon can then use the instruments to locate the positions of the original defect landmarks and evaluate the clinical results achieved through the treatment.

Although the technique of the present invention has been described above with respect to an arthroscopic procedure, it should be understood that the instruments and technique of the present invention can also be used with more invasive surgical procedures, such as a mini-arthrotomy or an open surgical procedure.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A method of mapping a tissue feature of a tissue site of a patient with a surgical instrument wherein the tissue site is a meniscus, the tissue feature having a position, the surgical instrument including a tube and a ruler reciprocable with respect to the tube between a retracted position and an extended position, the ruler including a distal end and distance indicia, the method comprising:
   moving a portion of the tube to the tissue site with at least part of the ruler retracted;
   piercing the tissue site with a portion of the ruler at a selected fixation point to temporarily anchor the distal end of the ruler to the tissue at the fixation point;
   with the distal end of the ruler anchored to the tissue at the fixation point, moving the tube with respect to the ruler so that the ruler is in the extended position;
   determining a distance based on a position of the tissue feature with respect to the fixation point; and
   moving the tube with respect to the ruler so that the ruler is in the retracted position and removing the tube and ruler from the tissue site.

2. A method of mapping a tissue feature of a tissue site of a patient with a surgical instrument, the tissue feature having a position, the surgical instrument including a tube and a ruler reciprocable with respect to the tube between a retracted position and an extended position, the ruler including a distal end and distance indicia, the method comprising:
   moving a portion of the tube to the tissue site with at least part of the ruler retracted;
   piercing the tissue site with a portion of the ruler at a selected fixation point to temporarily anchor the distal end of the ruler to the tissue at the fixation point;
   with the distal end of the ruler anchored to the tissue at the fixation point, moving the tube with respect to the ruler so that the ruler is in the extended position;
   determining a distance based on a position of the tissue feature with respect to the fixation point;
   moving the tube with respect to the ruler so that the ruler is in the retracted position and removing the tube and ruler from the tissue site;
   providing a second surgical instrument including a tube and a ruler reciprocable with respect to the tube between a retracted position and an extended position, the ruler including a distal end and distance indicia;
   moving a portion of the tube of the second instrument to the tissue site with at least part of the ruler retracted;
   fixing an end of the ruler to the tissue site at a second location spaced from the fixation point;
   moving the tube of the second instrument with respect to the ruler so that the ruler is in the extended position and wherein a portion of the ruler of the second instrument crosses a portion of the ruler of the first instrument;
   determining a distance based on a position of the ruler of the second instrument with respect to the ruler of the first instrument; and
   moving the tube with respect to the ruler so that the ruler is in the retracted position and removing the tube and ruler from the tissue site.

3. The method of claim 1 further comprising moving the portion of the tube to the tissue site a second time, guiding the tube to the tissue site with at least part of the ruler in the retracted position, moving the ruler to the extended position, piercing the tissue site at a a second fixation point to temporarily anchor the distal end of the ruler to the second fixation point; determining a second location based on a position of part of the ruler with respect to the second fixation point and moving the ruler to the retracted position and removing the tube and ruler from the tissue site.

4. The method of claim 3 wherein the second fixation point is substantially the same as the fixation point.

5. A method of measuring a tissue feature of a tissue site within the body of a patient with a surgical instrument wherein the tissue site is a meniscus,
   the surgical instrument including a tube having a proximal end and a distal end, an elongated member reciprocable with respect to the tube between a distally retracted position and a distally extended position, the elongated member having a proximal end and a distal end, and distance indicia at the proximal end of the elongated member, the method comprising:
   moving the distal end of the tube to the tissue site within the body of the patient;
   piercing the tissue site with the distal end of the elongated member at a first location, thereby temporarily anchoring the elongated member to the tissue site;

moving the tube with respect to the elongated member so that the distal end of the tube is at a second location while the distal end of the elongated member is maintained at the first location;

determining a distance between the first location and the second location by observing the distance indicia at the proximal end of the elongated member.

6. The method of claim 5 wherein the elongated member comprises an assembly of a ruler at the distal end and a shaft at the proximal end.

7. The method of claim 5 wherein the proximal end of the elongated member is maintained outside of the patient.

8. A method of mapping a tissue feature of a tissue site of a patient, wherein the tissue site is a meniscus, with a surgical coordinate instrument and a surgical measuring instrument, the surgical coordinate instrument including a tube and a coordinate ruler reciprocable with respect to the tube between a retracted position and an extended position, the coordinate ruler including a distal end and distance indicia, the surgical measuring instrument including a tube and a ruler reciprocable with respect to the tube between a retracted position and an extended position, the ruler including a distal end and distance indicia, the method comprising:

moving a portion of the tube of the coordinate instrument to the tissue site with at least part of the coordinate ruler retracted, piercing the tissue with a portion of the coordinate ruler at a selected fixation point to temporarily anchor the distal end of the coordinate ruler to the tissue at the fixation point, moving the tube with respect to the coordinate ruler so that the coordinate ruler is in the extended position;

moving a portion of the tube of the measuring instrument to the tissue site with at least part of the ruler retracted, placing the distal end of the ruler at a second location related to the feature to be mapped, moving the tube with respect to the ruler until a portion of the measuring instrument crosses the coordinate ruler;

determining a distance between a portion of the surgical measuring instrument and the coordinate ruler.

9. The method of claim 8 wherein the step of determining the distance between a portion of the surgical measuring instrument and the coordinate ruler comprises determining the distance between the hook and a location on the coordinate ruler.

10. The method of claim 8 wherein the feature to be mapped comprises a defect and wherein the second location for placement of the distal end of the ruler of the measuring instrument comprises a portion of the defect.

* * * * *